United States Patent
Boudreaux et al.

(10) Patent No.: US 11,020,200 B2
(45) Date of Patent: Jun. 1, 2021

(54) SURGICAL INSTRUMENT WITH DUAL MODE END EFFECTOR AND COMPOUND LEVER WITH DETENTS

(71) Applicant: Ethicon Endo-Surgery, LLC, Guaynabo, PR (US)

(72) Inventors: Chad P. Boudreaux, Cincinnati, OH (US); Monica L. Zeckel, Zionsville, IN (US)

(73) Assignee: Ethicon LLC, Guaynabo, PR (US)

(*) Notice: Subject to any disclaimer, the term of this patent is extended or adjusted under 35 U.S.C. 154(b) by 1166 days.

(21) Appl. No.: 15/284,837

(22) Filed: Oct. 4, 2016

(65) Prior Publication Data
US 2017/0105755 A1    Apr. 20, 2017

Related U.S. Application Data

(60) Provisional application No. 62/363,411, filed on Jul. 18, 2016, provisional application No. 62/243,189, filed on Oct. 19, 2015.

(51) Int. Cl.
*A61B 90/00* (2016.01)
*A61B 18/14* (2006.01)
(Continued)

(52) U.S. Cl.
CPC .......... *A61B 90/04* (2016.02); *A61B 17/2804* (2013.01); *A61B 17/285* (2013.01);
(Continued)

(58) Field of Classification Search
CPC ........ A61B 2090/034; A61B 2090/035; A61B 2090/0427; A61B 2090/0436;
(Continued)

(56) References Cited

U.S. PATENT DOCUMENTS 5,322,055 A    6/1994  Davison et al.
5,465,894 A    11/1995 Clark et al.
(Continued)

FOREIGN PATENT DOCUMENTS

CN    1694649 A    11/2005
CN    2820104 Y    9/2006
(Continued)

OTHER PUBLICATIONS

European Search Report and Written Opinion, Under Rule 164(2)(b) EPC, dated Oct. 29, 2019 for Application No. EP 16784766.4, 11 pgs.
(Continued)

*Primary Examiner* — Ronald Hupczey, Jr.
*Assistant Examiner* — Bradford C. Blaise
(74) *Attorney, Agent, or Firm* — Frost Brown Todd LLC

(57) ABSTRACT

A surgical instrument includes a body, an ultrasonic blade, a clamp arm assembly, and a detent assembly. The clamp arm assembly includes a clamp arm pivotably coupled with the body at a pivot assembly. The clamp arm is operable to compress tissue against the ultrasonic blade. The detent assembly is configured to provide tactile resistance to pivotal movement of the clamp arm relative to the body beyond a predefined pivot angle. The detent assembly is configured to permit pivotal movement of the clamp arm relative to the body beyond a predefined pivot angle upon application of a force sufficient to overcome the tactile resistance.

20 Claims, 36 Drawing Sheets

(51) Int. Cl.
*A61B 17/28* (2006.01)
*A61B 17/285* (2006.01)
*A61B 17/29* (2006.01)
*A61B 17/295* (2006.01)
*A61B 17/32* (2006.01)
*A61B 18/00* (2006.01)
*A61B 17/00* (2006.01)

(52) U.S. Cl.
CPC ...... *A61B 17/2812* (2013.01); *A61B 17/2816* (2013.01); *A61B 17/2833* (2013.01); *A61B 17/2841* (2013.01); *A61B 17/29* (2013.01); *A61B 17/295* (2013.01); *A61B 17/320092* (2013.01); *A61B 18/14* (2013.01); *A61B 18/1442* (2013.01); *A61B 18/1445* (2013.01); *A61B 90/03* (2016.02); *A61B 2017/00022* (2013.01); *A61B 2017/00026* (2013.01); *A61B 2017/0046* (2013.01); *A61B 2017/00119* (2013.01); *A61B 2017/00123* (2013.01); *A61B 2017/00128* (2013.01); *A61B 2017/00464* (2013.01); *A61B 2017/00477* (2013.01); *A61B 2017/00778* (2013.01); *A61B 2017/00818* (2013.01); *A61B 2017/2825* (2013.01); *A61B 2017/2829* (2013.01); *A61B 2017/2931* (2013.01); *A61B 2017/2933* (2013.01); *A61B 2017/2939* (2013.01); *A61B 2017/2944* (2013.01); *A61B 2017/2946* (2013.01); *A61B 2017/2947* (2013.01); *A61B 2017/320093* (2017.08); *A61B 2017/320094* (2017.08); *A61B 2017/320095* (2017.08); *A61B 2018/0019* (2013.01); *A61B 2018/0063* (2013.01); *A61B 2018/0094* (2013.01); *A61B 2018/00178* (2013.01); *A61B 2018/00297* (2013.01); *A61B 2018/00309* (2013.01); *A61B 2018/00345* (2013.01); *A61B 2018/00529* (2013.01); *A61B 2018/00589* (2013.01); *A61B 2018/00601* (2013.01); *A61B 2018/00702* (2013.01); *A61B 2018/00708* (2013.01); *A61B 2018/00767* (2013.01); *A61B 2018/00875* (2013.01); *A61B 2018/00892* (2013.01); *A61B 2018/00898* (2013.01); *A61B 2018/00916* (2013.01); *A61B 2018/00922* (2013.01); *A61B 2018/00928* (2013.01); *A61B 2018/00958* (2013.01); *A61B 2018/00988* (2013.01); *A61B 2018/00994* (2013.01); *A61B 2018/1405* (2013.01); *A61B 2018/146* (2013.01); *A61B 2018/1455* (2013.01); *A61B 2018/1467* (2013.01); *A61B 2090/035* (2016.02); *A61B 2090/036* (2016.02); *A61B 2090/0427* (2016.02); *A61B 2090/0436* (2016.02); *A61B 2090/0472* (2016.02); *A61B 2090/0481* (2016.02); *A61B 2090/064* (2016.02); *A61B 2090/0803* (2016.02); *A61B 2090/0808* (2016.02); *A61B 2090/0811* (2016.02); *A61B 2090/0812* (2016.02); *A61B 2090/0813* (2016.02); *A61B 2090/0814* (2016.02)

(58) Field of Classification Search
CPC .... A61B 2090/0472; A61B 2090/0481; A61B 90/04; A61B 17/2804; A61B 17/2812; A61B 17/2816; A61B 17/320092; A61B 2017/2931; A61B 2017/2939; A61B 2017/2944; A61B 2017/2947; A61B 2017/320093; A61B 2017/320094; A61B 2017/320095; A61B 18/1442; A61B 18/146; A61B 2018/0019; A61B 2018/00297; A61B 2018/00309; A61B 2018/00994

See application file for complete search history.

(56) References Cited

U.S. PATENT DOCUMENTS

| | | |
|---|---|---|
| 5,556,404 A | 9/1996 | Belanger et al. |
| 5,607,094 A | 3/1997 | Clark et al. |
| 5,797,939 A * | 8/1998 | Yoon ............... A61B 17/122 |
| | | 606/167 |
| 5,827,299 A | 10/1998 | Thomason et al. |
| 5,873,873 A | 2/1999 | Smith et al. |
| 5,980,510 A | 11/1999 | Tsonton et al. |
| 6,325,811 B1 | 12/2001 | Messerly |
| 6,454,781 B1 * | 9/2002 | Witt ............... A61B 17/320092 |
| | | 606/169 |
| 6,773,444 B2 | 8/2004 | Messerly |
| 6,783,524 B2 | 8/2004 | Anderson et al. |
| 7,267,677 B2 | 9/2007 | Johnson et al. |
| 7,563,269 B2 | 7/2009 | Hashiguchi |
| 8,461,744 B2 | 6/2013 | Wiener et al. |
| 8,591,536 B2 | 11/2013 | Robertson |
| 8,623,027 B2 | 1/2014 | Price et al. |
| 8,845,667 B2 | 9/2014 | Cruz Hernandez et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,375,255 B2 | 6/2016 | Houser et al. |
| 9,381,058 B2 | 7/2016 | Houser et al. |
| 9,393,037 B2 | 7/2016 | Olson et al. |
| 9,610,115 B2 | 4/2017 | Rothweiler et al. |
| 10,004,528 B2 | 6/2018 | Faller et al. |
| 2004/0093020 A1 | 5/2004 | Sinton |
| 2005/0192612 A1 * | 9/2005 | Houser ........... A61B 17/320092 |
| | | 606/169 |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0255130 A1 | 10/2009 | Jalmberger |
| 2009/0261804 A1 | 10/2009 | McKenna et al. |
| 2009/0299367 A1 | 12/2009 | Ginnebaugh et al. |
| 2010/0063525 A1 * | 3/2010 | Beaupre ........... A61B 17/320092 |
| | | 606/169 |
| 2010/0331873 A1 | 12/2010 | Dannaher et al. |
| 2011/0290853 A1 | 12/2011 | Shelton, IV et al. |
| 2012/0116265 A1 | 5/2012 | Houser et al. |
| 2012/0116391 A1 | 5/2012 | Houser et al. |
| 2012/0245582 A1 | 9/2012 | Kimball et al. |
| 2013/0110155 A1 | 5/2013 | Tsuchiya et al. |
| 2013/0303949 A1 | 11/2013 | Kawaguchi et al. |
| 2013/0345732 A1 | 12/2013 | Dannaher et al. |
| 2014/0066911 A1 | 3/2014 | Nau, Jr. |
| 2014/0135804 A1 * | 5/2014 | Weisenburgh, II .... A61B 17/29 |
| | | 606/169 |
| 2014/0330298 A1 | 11/2014 | Arshonsky et al. |
| 2015/0080924 A1 | 3/2015 | Stulen et al. |
| 2015/0080925 A1 | 3/2015 | Schulte et al. |
| 2015/0148833 A1 | 5/2015 | Stokes et al. |
| 2015/0196782 A1 | 7/2015 | Akagane |
| 2015/0305796 A1 | 10/2015 | Wang |
| 2015/0313667 A1 * | 11/2015 | Allen, IV ....... A61B 17/320092 |
| | | 606/51 |
| 2015/0342583 A1 | 12/2015 | Van De Weghe et al. |
| 2016/0045770 A1 | 2/2016 | Yamada |
| 2016/0199121 A1 | 7/2016 | Kase |
| 2017/0105788 A1 | 4/2017 | Boudreaux et al. |

FOREIGN PATENT DOCUMENTS

| | | |
|---|---|---|
| CN | 101820825 A | 9/2010 |
| CN | 103561664 A | 2/2014 |
| CN | 104271051 A | 1/2015 |
| DE | 298 11 977 U1 | 10/1998 |
| EP | 1769765 A1 | 4/2007 |

(56) References Cited

FOREIGN PATENT DOCUMENTS

| EP | 2 436 328 A1 | 4/2012 |
|---|---|---|
| EP | 2 589 347 A1 | 5/2013 |
| JP | 2005-176905 A | 7/2005 |
| JP | 2010-264258 A | 11/2010 |
| JP | 2014-226318 A | 12/2014 |
| WO | WO 02/080798 A1 | 10/2002 |
| WO | WO 2009/149799 A1 | 12/2009 |
| WO | WO 2013/154923 A2 | 10/2013 |
| WO | WO 2013/115036 A1 | 5/2015 |
| WO | WO 2015/107916 A1 | 7/2015 |
| WO | WO 2016/044277 A1 | 3/2016 |

OTHER PUBLICATIONS

European Examination Report dated Aug. 1, 2019 for Application No. EP 16798019.2, 5 pgs.
European Search Report, Partial, and Provisional Written Opinion dated Aug. 2, 2019 for Application No. EP 19185531.1, 13 pgs.
European Search Report and Written Opinion dated Nov. 4, 2019 for Application No. EP 19185531.1, 12 pgs.
European Search Report, Partial, and Provisional Written Opinion dated Aug. 5, 2019 for Application No. EP 19185541.0, 12 pgs.
European Search Report and Written Opinion dated Oct. 30, 2019 for Application No. EP 19185541.0, 14 pgs.
U.S. Appl. No. 61/410,603, filed Nov. 5, 2010.
U.S. Appl. No. 62/243,189, filed Oct. 19, 2015.
U.S. Appl. No. 62/363,411, filed Jul. 18, 2016.
U.S. Appl. No. 15/284,819, filed Oct. 4, 2016.
U.S. Appl. No. 15/284,837, filed Oct. 4, 2016.
International Search Report and Written Opinion dated Mar. 3, 2017 for Application No. PCT/US2016/057277, 18 pgs.
International Search Report and Written Opinion dated Mar. 30, 2017 for Application No. PCT/US2016/057280, 19 pgs.
International Search Report and Written Opinion dated Feb. 6, 2017 for Application No. PCT/US2016/057288, 14 pgs.
U.S. Pat. Pub. No. 2017/0105754.
U.S. Pat. Pub. No. 2017/0105788.
Chinese Office Action dated May 27, 2020 for Application No. 201680061293.1, 14 pages.
U.S. Appl. No. 15/284,819.
U.S. Appl. No. 15/284,855.
Chinese Office Action, The First Office Action, and First Search, dated Jun. 2, 2020, for Application No. CN 201680061050.8, 18 pgs.
Chinese Office Action, The First Office Action, and First Search, dated Jun. 2, 2020, for Application No. CN 201680061406.8, 20 pgs.
European Examination Report dated Aug. 2, 2019 for Application No. EP 16784766.4, 7 pgs.
Japanese Office Action, Notice of Reasons for Refusal, Search Report by Registered Search Organization, dated Oct. 6, 2020 for Application No. JP 2018-539244, 23 pgs.
Japanese Office Action, Notice of Reasons for Refusal, Search Report by Registered Search Organization, dated Oct. 6, 2020 for Application No. JP 2018-539245, 22 pgs.
Japanese Office Action, Notice of Reasons for Refusal, Search Report by Registered Search Organization, dated Oct. 6, 2020 for Application No. JP 2018-539246, 22 pgs.

* cited by examiner

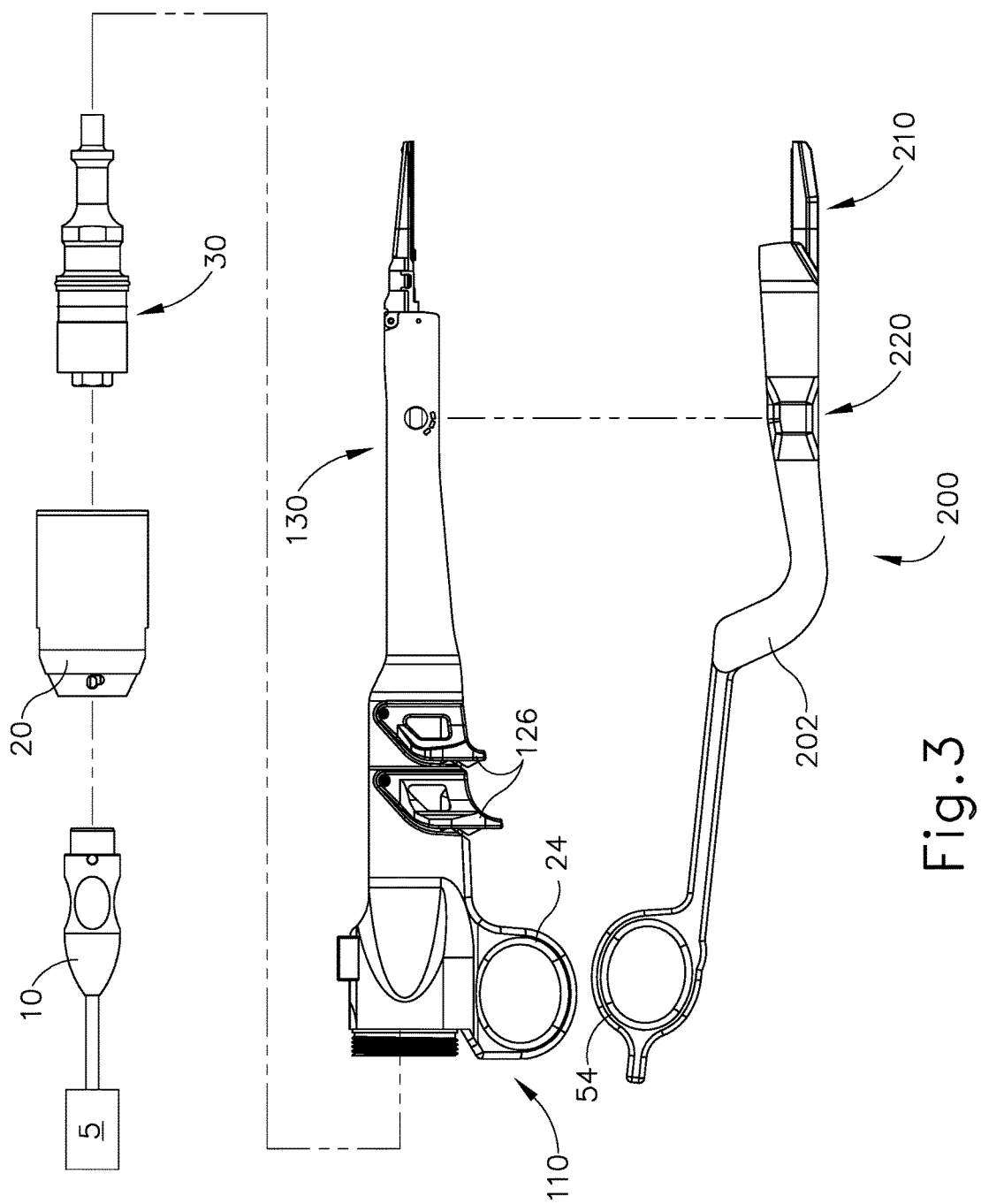

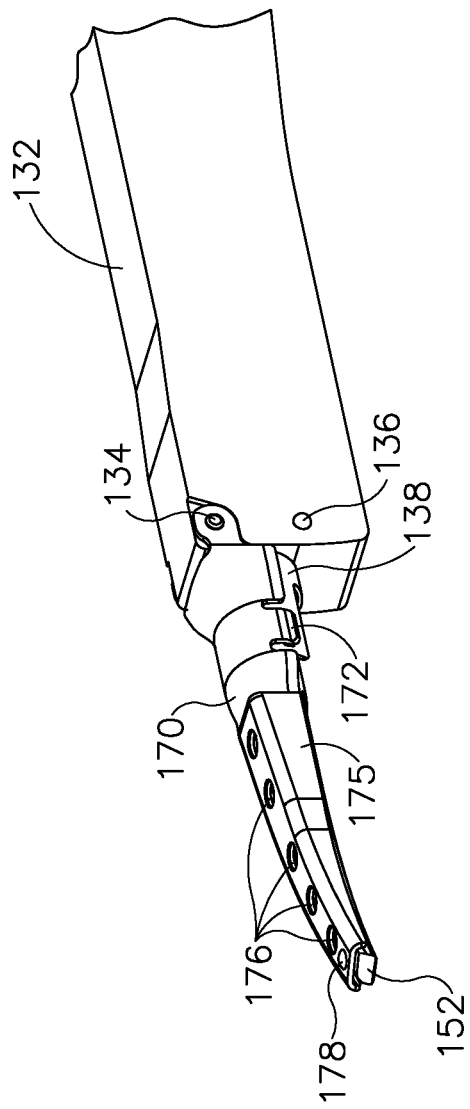

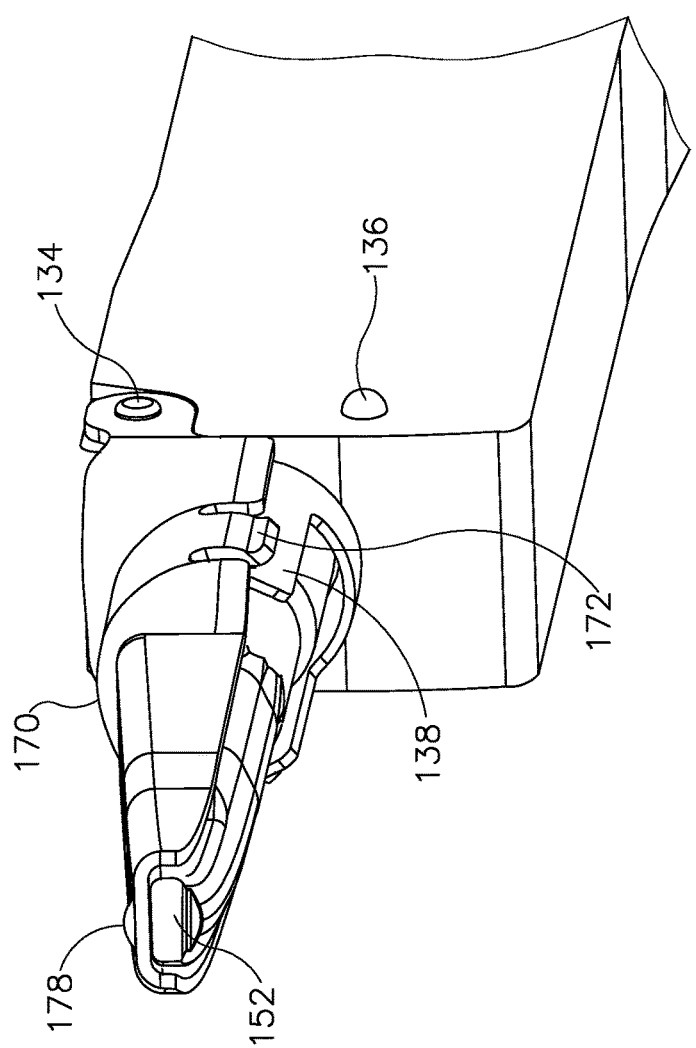

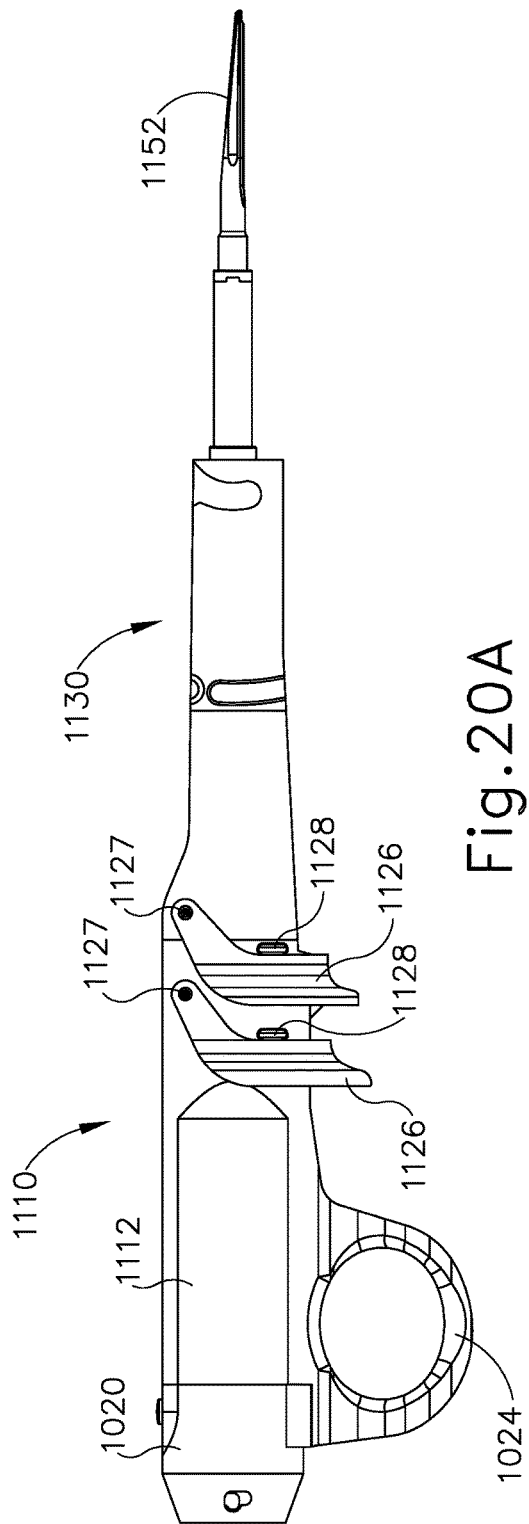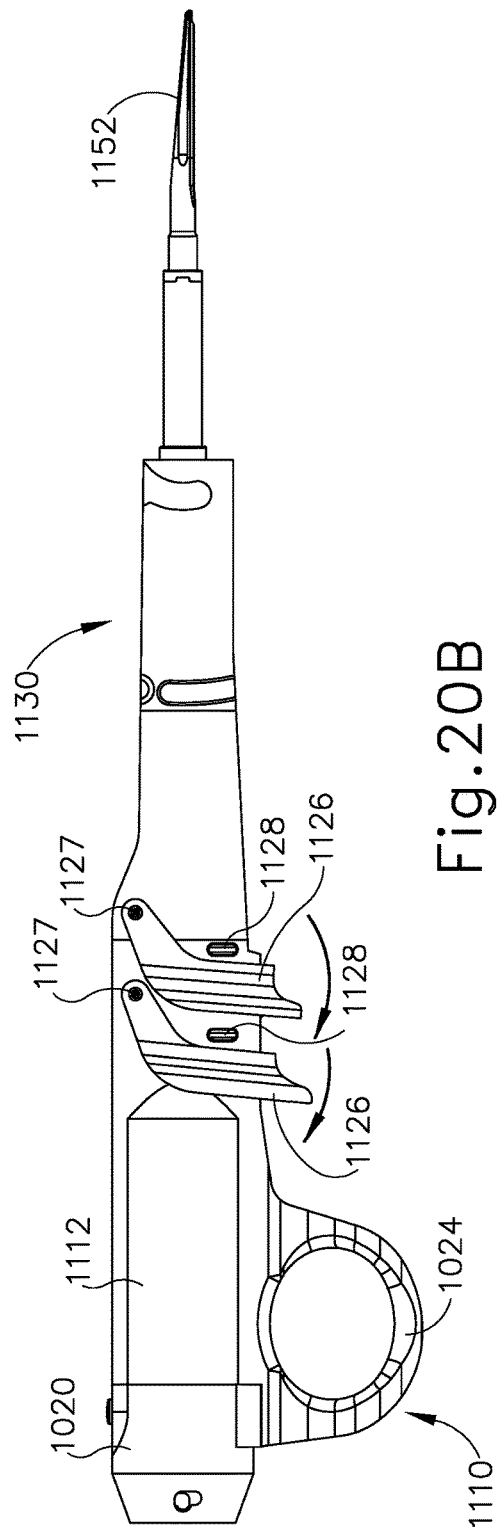

SURGICAL INSTRUMENT WITH DUAL MODE END EFFECTOR AND COMPOUND LEVER WITH DETENTS

PRIORITY

This application claims priority to U.S. Provisional Patent App. No. 62/363,411, entitled "Surgical Instrument with Dual Mode End Effector," filed Jul. 18, 2016, the disclosure of which is incorporated by reference herein.

This application also claims priority to U.S. Provisional Patent App. No. 62/243,189, entitled "Surgical Instrument with Dual Mode End Effector," filed Oct. 19, 2015, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts an exploded view of the instrument of FIG. 1A;

FIG. 8B depicts a perspective view of the ultrasonic blade of FIG. 6 and the heat shield of FIG. 5, with the heat shield pivoted to a downward position;

FIG. 9 depicts another perspective view of the ultrasonic blade of FIG. 6 and the heat shield of FIG. 5, with the heat shield in the downward position;

FIG. 20A depicts a side elevational view of the handle assembly of the instrument of FIG. 11A, with both of the triggers in respective first pivotal positions;

FIG. 20B depicts a side elevational view of the handle assembly of the instrument of FIG. 11A, with both of the triggers in respective second pivotal positions;

Figure 1A:
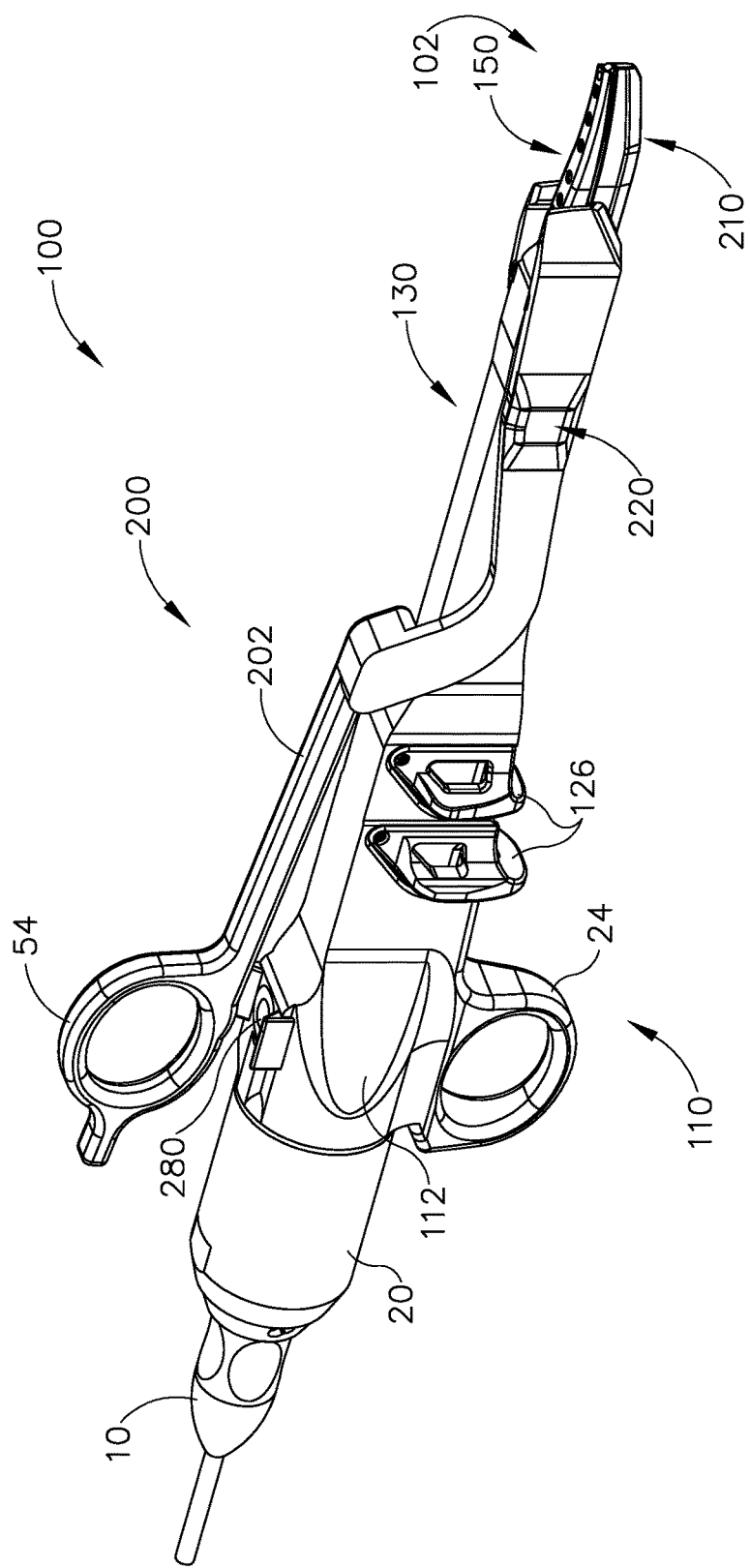
FIG. 1A depicts a perspective view of an exemplary surgical instrument, with an end effector of the instrument in a closed configuration.
Figure 1B:
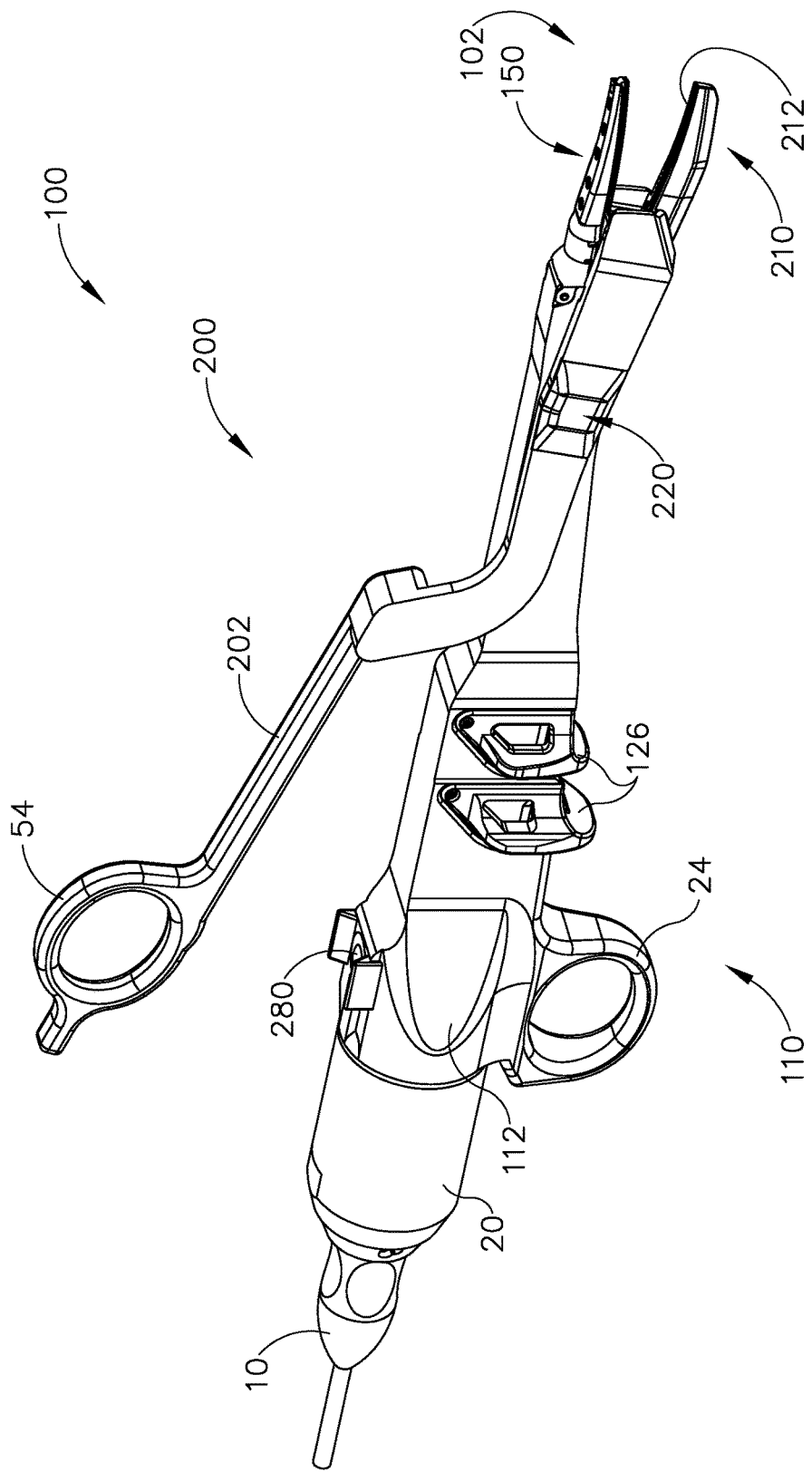
FIG. 1B depicts a perspective view of the instrument of FIG. 1A, with the end effector in an open configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc.

described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. EXEMPLARY ULTRASONIC SURGICAL INSTRUMENT FOR OPEN SURGICAL PROCEDURES

A. Overview

FIGS. 1A-3 illustrate exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U. S. Pub. No. 2008/0200940, now abandoned; U. S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a plug (10), a proximal casing (20), handle assembly (110), a shaft assembly (130), a blade assembly (150), a clamp arm assembly (200), and an end effector (102). As will be described in greater detail below, clamp arm assembly (200) may be selectively attached to handle assembly (110) and detached from handle assembly (110). The ability to selectively attach and detach clamp arm assembly (200) from handle assembly (110) may provide additional benefits of reusability for either handle assembly (110) or clamp arm assembly (200).

Handle assembly (110) comprises a body (112) including a finger grip ring (24), a button (280) on top of body (112), and a pair of buttons (126) distal to finger grip ring (24). Instrument (100) also includes a clamp arm assembly (200) that is pivotable toward and away from body (122). Clamp arm assembly (200) includes a body (202) with a thumb grip ring (54). Thumb grip ring (54) and finger grip ring (24) together provide a scissor grip type of configuration. It should be understood, however, that various other suitable configurations may be used, including but not limited to a pistol grip configuration.

Figure 2A:
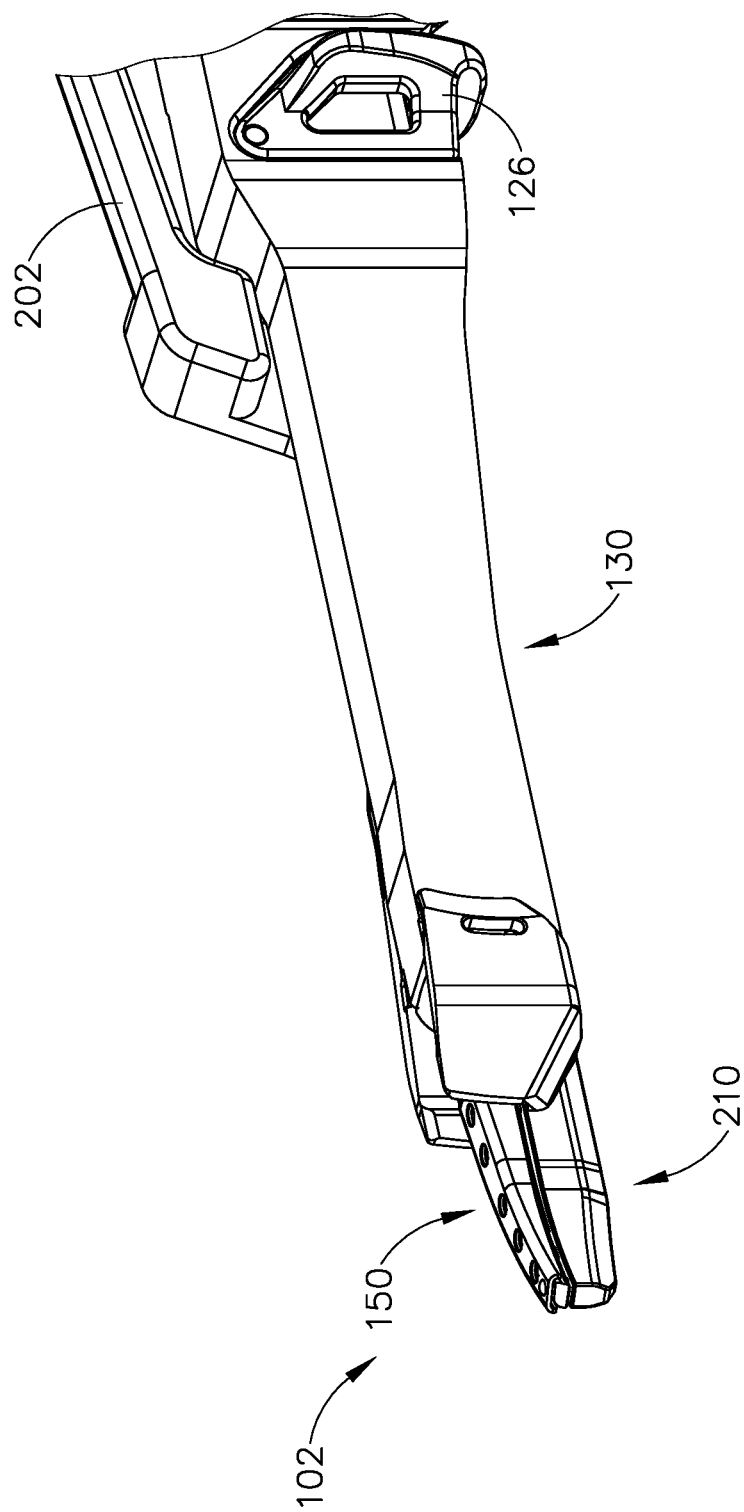
FIG. 2A depicts an enlarged perspective view of the end effector of FIG. 1A in a closed configuration.
Figure 2B:
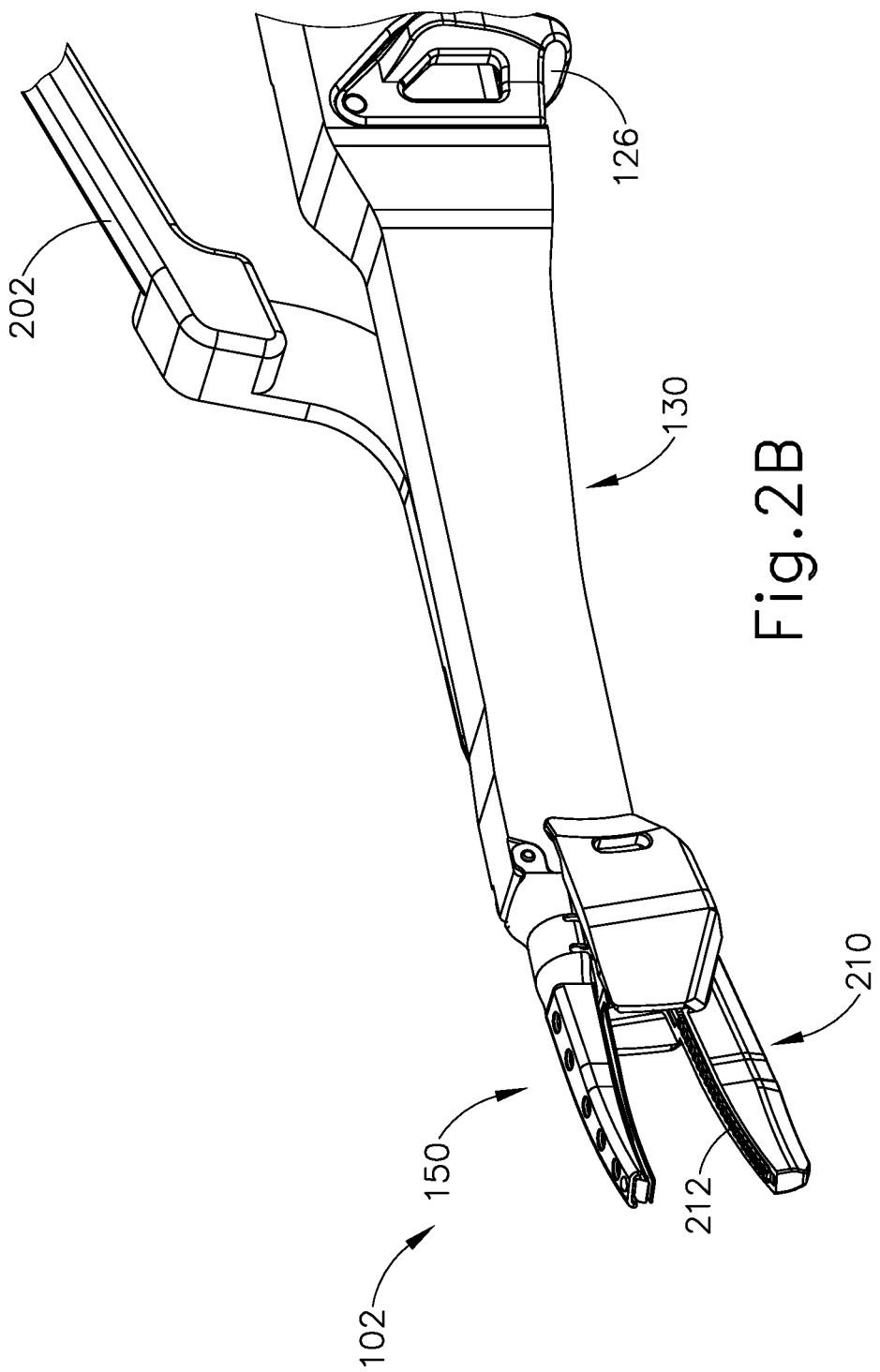
FIG. 2B depicts an enlarged perspective view of the end effector of FIG. 1A in an open configuration.

Shaft assembly (130) comprises an outer sheath (132) extending distally from body (112). As best seen in FIGS. 2A-2B, end effector (102) comprises an ultrasonic blade (142) and a clamp pad assembly (210). End effector (102) is operable to transition between a closed position, as shown in FIG. 2A, and an open position, as show in FIG. 2B. Ultrasonic blade (142) extends distally from outer sheath (132). As will be described in greater detail below, ultrasonic blade (142) is a part of blade assembly (150).

Clamp pad assembly (210) is an integral feature of clamp arm assembly (200). Clamp pad assembly (210) includes a clamp pad (212) facing ultrasonic blade (142). In some versions, clamp pad assembly further includes one or more electrodes that is/are operable to apply RF electrosurgical energy to tissue. Clamp pad assembly (210) is pivotally coupled with outer sheath (132) via a coupling assembly (220). Clamp pad assembly (210) is positioned distal to coupling assembly (220); while body (202) and thumb grip ring (154) are positioned proximal to coupling assembly (220). Thus, as shown in FIGS. 1A-2B, clamp pad assembly (210) is pivotable toward and away from ultrasonic blade (142) based on pivoting of thumb grip ring (54) toward and away from body (112) of handle assembly (110). It should therefore be understood that an operator may squeeze thumb grip ring (54) toward body (112) to thereby clamp tissue between clamp pad assembly (210) and ultrasonic blade (142) to compress tissue against ultrasonic blade (142). When ultrasonic blade (142) is activated during such compression, clamp pad assembly (210) and ultrasonic blade (142) cooperate to transect and/or seal the compressed tissue. In some versions, one or more resilient members are used to bias clamp pad assembly (210) to the open position shown in FIGS. 1B and 2B. By way of example only, such a resilient member may comprise a leaf spring, a torsion spring, and/or any other suitable kind of resilient member.

Referring to FIG. 3, an ultrasonic transducer assembly (30) is housed within proximal casing (20) and body (112) of handle assembly (110). Transducer assembly (30) is coupled with a generator (5) via a plug (10). Transducer assembly (30) receives electrical power from generator (5) and converts that power into ultrasonic vibrations through piezoelectric principles. Generator (5) may include a power source and control module that is configured to provide a power profile to transducer assembly (30) that is particularly suited for the generation of ultrasonic vibrations through transducer assembly (30). Generator (5) may also be configured to provide a power profile that enables end effector (102) to apply RF electrosurgical energy to tissue.

By way of example only, generator (5) may comprise a GEN 300 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (5) may be integrated into handle assembly (110), and that handle assembly (110) may even include a battery or other on-board power source such that plug (10) is omitted. Still other suitable forms that generator (5) may take, as well as various features and operabilities that generator (5) may provide, will be apparent to those of ordinary skill in the art in view of the teachings herein.

Ultrasonic vibrations that are generated by transducer assembly (30) are communicated along an acoustic waveguide (154). Waveguide (154) is mechanically and acoustically coupled with transducer assembly (30). Waveguide (154) extends through shaft assembly (130) to reach ultrasonic blade (152). Waveguide (154) is secured within shaft assembly (130) via locator pins (134, 136), which will be described in greater detail below. Pins (134, 136) are located at a position along the length of waveguide (154) corresponding to a node associated with resonant ultrasonic vibrations communicated through waveguide (154). As noted above, when ultrasonic blade (152) is in an activated state (i.e., vibrating ultrasonically), ultrasonic blade (152) is operable to effectively cut through and seal tissue, particularly when the tissue is being clamped between clamp pad (212) and ultrasonic blade (142). It should be understood that waveguide (154) may be configured to amplify mechanical vibrations transmitted through waveguide (154). Furthermore, waveguide (154) may include features operable to control the gain of the longitudinal vibrations along waveguide (154) and/or features to tune waveguide (154) to the resonant frequency of the system.

In the present example, the distal end of ultrasonic blade (152) is located at a position corresponding to an anti-node associated with resonant ultrasonic vibrations communicated through waveguide (154), in order to tune the acoustic assembly to a preferred resonant frequency $f_o$ when the acoustic assembly is not loaded by tissue. When transducer assembly (30) is energized, the distal end of ultrasonic blade (152) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through the waveguide to reach ultrasonic blade (152), thereby providing oscillation of ultrasonic blade (152) at the resonant ultrasonic frequency. Thus, when tissue is secured between ultrasonic blade (152) and clamp pad (212), the ultrasonic oscillation of ultrasonic blade (152) may simultaneously sever the tissue and denature the proteins in adjacent tissue cells, thereby providing a coagulative effect with relatively little thermal spread. In some versions, an electrical current may also be provided through ultrasonic blade (152) and/or clamp pad (212) to also seal the tissue.

As will be described in greater detail below, instrument (100) is also configured to provide radiofrequency (RF) energy to a surgical site via end effector (102). By way of example only, an operator may rely mainly on the use of ultrasonic energy from blade (152) to sever tissue that is captured between ultrasonic blade (152) and clamp pad (212). The operator may further rely on the use of RF energy from end effector (102) to seal the severed tissue. Of course, it will be understood that the ultrasonic energy from blade (152) may seal tissue to some degree, such that the RF energy from end effector (102) may supplement the sealing that would already be provided from the ultrasonic energy. It will also be understood that there may be instances where the operator may wish to simply wish to use end effector (102) to only apply RF energy to tissue, without also applying ultrasonic energy to tissue. As will be appreciated from the description herein, some versions of instrument (100) are capable of providing all of the above noted kinds of functionality.

An operator may activate buttons (126) to selectively activate transducer assembly (30) to thereby activate ultrasonic blade (152). In the present example, two buttons (126) are provided. In some versions, one button (126) is provided for activating ultrasonic blade (152) at a first power profile (e.g., a first frequency and/or first amplitude) and another button (126) is provided for activating ultrasonic blade (152) at a second power profile (e.g., a second frequency and/or second amplitude). In some other versions, one button (126) is provided for activating ultrasonic blade (152) with ultrasonic energy, and the other button (126) is provided for activating end effector (102) with RF energy. It should be understood that any other suitable number of buttons and/or otherwise selectable power levels and/or power modalities may be provided. For instance, a foot pedal may be provided to selectively activate transducer assembly (30).

Buttons (126) of the present example are positioned such that an operator may readily fully operate instrument (100) with a single hand. For instance, the operator may position their thumb in thumb grip ring (54), position their ring finger in finger grip ring (124), position their middle finger about body (112), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U. S. Pub. No. 2008/0200940, now abandoned; U. S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,0347 on Jun. 19, 2016; U.S. Pub. No. 2014/0114334, issued as U.S. Pat. No. 9,095,367 on Aug. 4, 2015; and/or U. S. Pub. No. 2015/0080925, entitled "Alignment Features for Ultrasonic Surgical Instrument," published Mar. 19, 2015, now abandoned, the disclosure of which is incorporated by reference herein. Additional merely illustrative features and variations for instrument (100) will be described in greater detail below. It should be understood that the below described variations may be readily incorporated into to instrument (100) described above and into any of the instruments described in any of the references that are cited herein, among others.

B. Exemplary Blade Assembly

Figure 4:
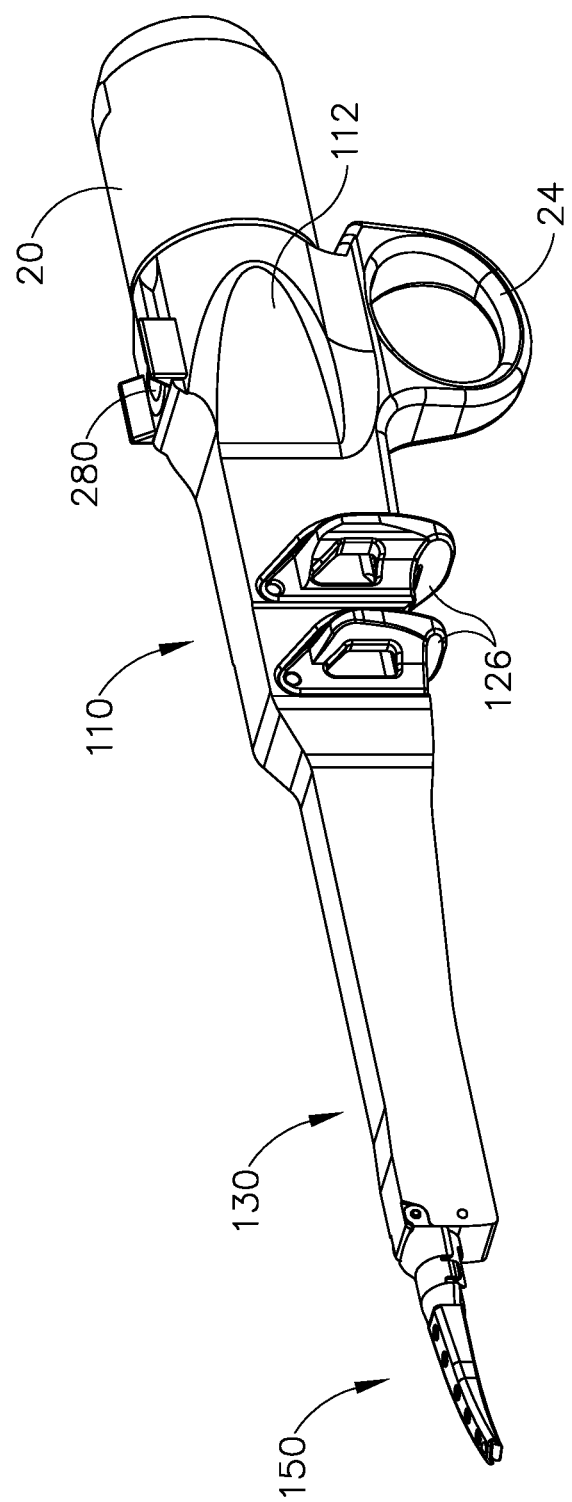
FIG. 4 depicts a perspective view of a handle assembly of the instrument of FIG. 1A.

FIG. 4 shows proximal casing (20), handle assembly (110), shaft assembly (130), and blade assembly (150) with clamp arm assembly (200) detached. As described above, it may be beneficial to have a clamp arm assembly (200) that may selectively detach from the rest of instrument (100) so that certain aspects of instrument (100) may be reusable while other features of instrument (100) are disposed of. In such case, the reusable aspects of instrument (100) will have to be cleaned and sterilized. Providing easy access to areas of instrument (100) that need to be cleaned and sterilized may ensure a thorough cleaning for the next surgical procedure.

Figure 5:
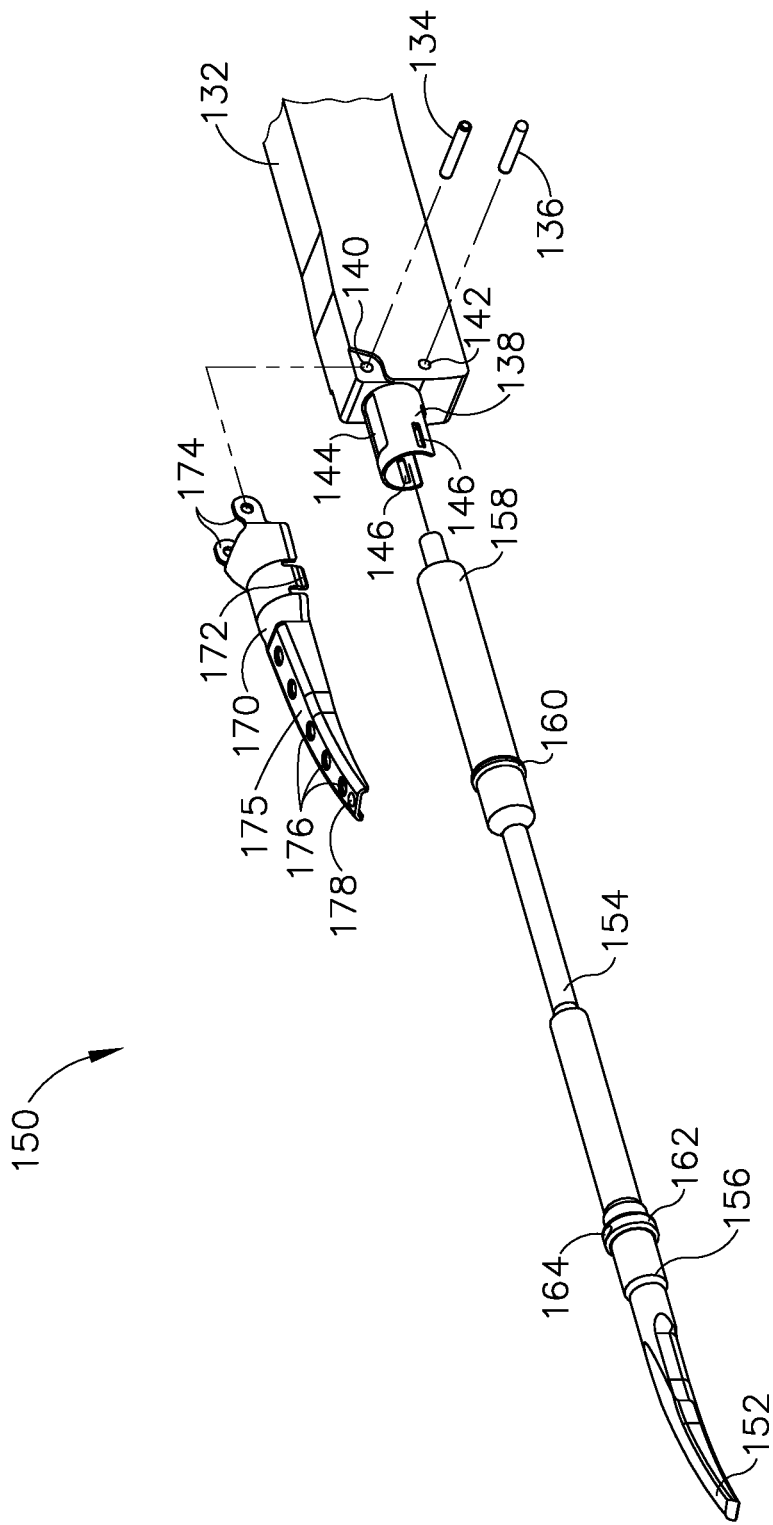
FIG. 5 depicts an exploded view showing a waveguide and heat shield separated from the distal end of the handle assembly of FIG. 4.

FIG. 5 shows a more detailed view of blade assembly (150). Blade assembly (150) includes ultrasonic blade (152), acoustic waveguide (154), and heat shield (170). As will be described in greater detail below, heat shield (170) is capable of pivoting from an unlocked position to a locked position. As also shown in FIG. 5, a tube (138) projects distally from the distal end of outer sheath (132).

Ultrasonic blade (152) is unitarily connected to acoustic waveguide (154).

Acoustic waveguide (154) includes a proximal end (158), a distal end (156), a proximal seal (160), and a distal seal (162). As described above, acoustic waveguide (154) communicates ultrasonic vibrations from transducer assembly (30) to ultrasonic blade (152). Acoustic waveguide (154) is housed within shaft assembly (130), more specifically within tube (138) of shaft assembly (130). Proximal seal (160) and distal seal (162) are each located at a respective position along the length of waveguide (154) corresponding to a respective node associated with resonant ultrasonic vibrations communicated through waveguide (154).

Proximal seal (160) and distal seal (162) are sized to abut against the interior of tube (138). Because proximal seal (160) and distal seal (162) are positioned along the length of waveguide (154) corresponding to nodes associated with resonant ultrasonic vibrations, contact between tube (138) and seals (160, 162) may not affect ultrasonic vibrations communication through waveguide (154). Interaction between distal seal (162) and tube (138) may prevent fluids from traveling proximally within tube (138) in relation to distal seal (162).

Figure 6:
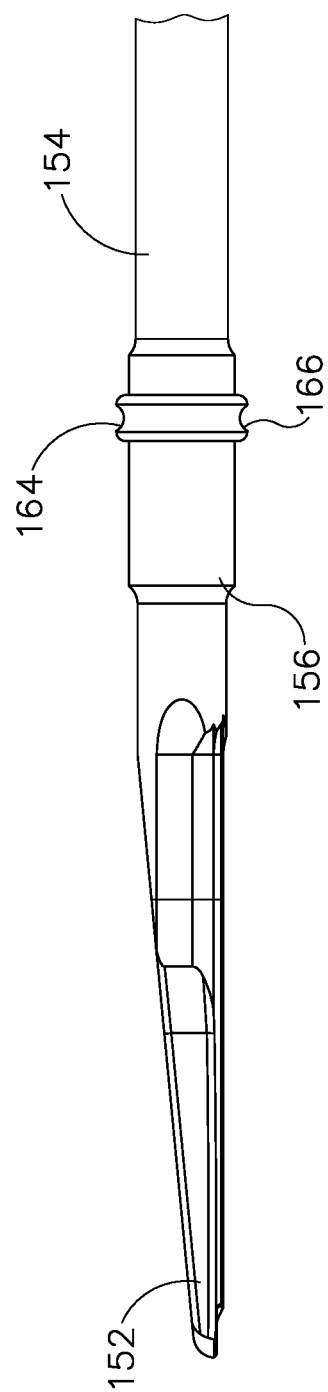
FIG. 6 depicts a side elevational view of an ultrasonic blade of the instrument of FIG. 1A.

As shown in FIG. 6, distal seal (162) includes an upper locking feature (164) and a lower locking feature (166), which are sized to receive locator pins (134, 136). In some versions, locking features (164, 166) are both defined by a single annular recess that extends about the circumferential perimeter of distal seal (162). In some other versions, locking features (164, 166) are formed as discrete scallops or recesses in distal seal (162). As can be seen in FIG. 5, outer sheath (132) includes upper and lower pin holes (140, 142) that are also sized to receive locator pins (134, 136).

Figure 7:
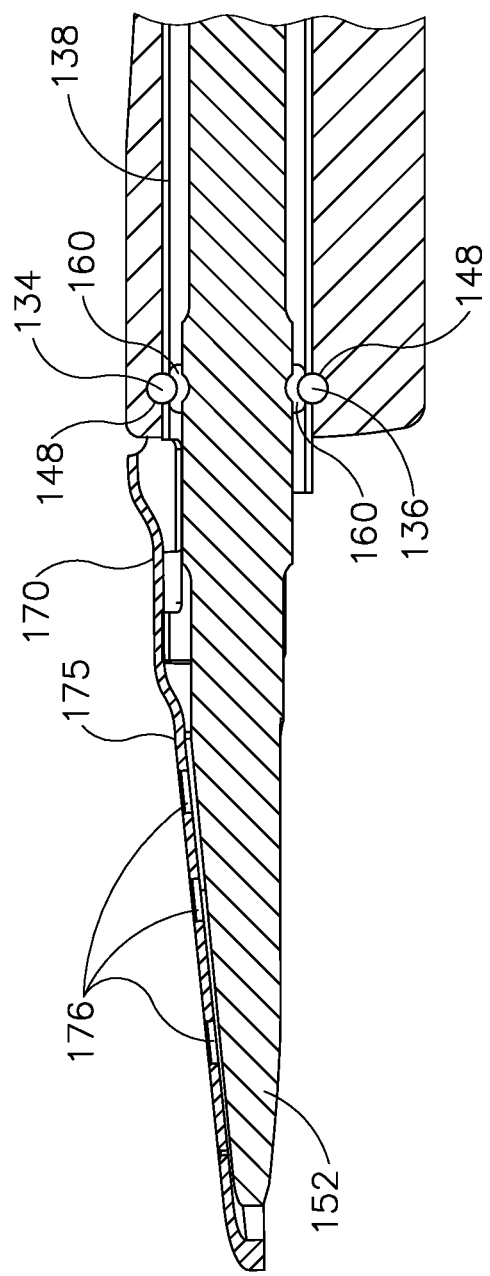
FIG. 7 depicts a cross-sectional side view of the ultrasonic blade of FIG. 6 and the heat shield of FIG. 5.

Distal seal (162) is located along waveguide (154) such that upper and lower locking features (164, 166) longitudinally align with upper and lower pin holes (140, 142) respectively, when waveguide (154) is fully seated in handle assembly (110). Additionally, as shown in FIG. 7, tube (138) includes slots (148) that are located within outer sheath (132). Slots (148) are positioned to align with upper and lower pin holes (140, 142) of outer sheath (132). Slots (148) are also sized and located along the length of tube (130) in order to receive locator pins (134, 136). Therefore, when acoustic waveguide (154) is housed within tube (138) and fully seated in handle assembly (110), locator pins (134, 136) may be inserted into upper and lower pin holes (140, 142), thereby entering slots (148) of tube (138) and making contact with upper locating feature (164) and lower locating feature (166), respectively. Contact between upper locating feature (164) and locator pin (134), as well as contact between lower locating feature (166) and locator pin (136) impart a frictional braking force on acoustic waveguide (154). This frictional braking force simultaneously prevents acoustic waveguide (154) from rotating about its own longitudinal axis and sliding longitudinally relative to outer sheath (132). Thus, interaction between locator pins (134, 136) and locating features (164, 166) may help acoustic waveguide (154) remain fixed relative to outer sheath (132). Locating features (164, 166) and locator pins (134, 136) may also help reduce tolerance stack between ultrasonic blade (152) and clamp arm assembly (200) due to the location of locating features (164, 166) being positioned close to the distal tip of ultrasonic blade (152).

FIGS. 5 and 8A-9 show heat shield (170) of the present example. As described above, heat shield (170) is capable of pivoting between an unlocked position (FIG. 8A) and a locked position (FIG. 8B). Heat shield (170) includes a pair of spring locks (172), a pair of coupling holes (174), an elongate body (175) that is sized to cover a portion of ultrasonic blade (152), a plurality of apertures (176) located along elongate body (175), and a distal bumper (178). Heat shield (170) may be metal sampled. Head shield (170) may also be coated with a non-stick, non-conductive coating, such as silicone, polytetrafluoroethylene (PTFE), and/or any other suitable material as will be apparent to those of ordinary skill in the art in view of the teachings herein. Because blade assembly (150) may be used multiple times, heat shield (170) may be durable in order to survive multiple uses, handling, and cleaning. By way of example only, heat shield (170) may be constructed in accordance with at least some of the teachings of U.S. Pub. No. 2015/0148833, entitled "Shielding Features for Ultrasonic Blade of a Surgical Instrument," published May 28, 2015, issued as U.S. Pat. No. 9,993,260 on Jun. 12, 2018, the disclosure of which is incorporated by reference herein.

Coupling holes (174) are spaced to align on the outside of upper pin hole (140). Coupling holes (174) are also sized to receive locator pin (134). When coupling holes (174) are aligned with pin hole (140), locator pin (134) may travel through coupling holes (174) and upper pin hole (140), thereby rotatably coupling heat shield (170) to outer sheath (132). Therefore, when assembled, heat shield (170) may rotate about the axis defined by locator pin (134), as shown in the series depicted in FIGS. 8A-8B.

Figure 8A:
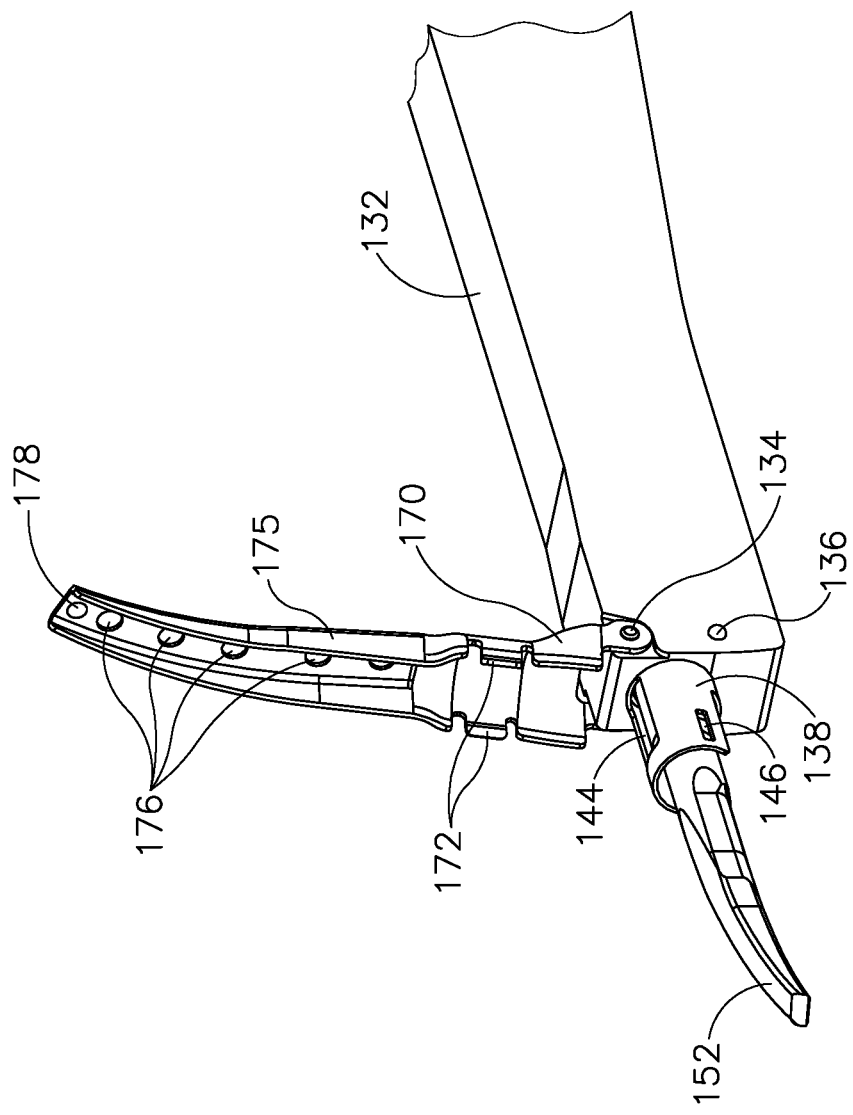
FIG. 8A depicts a perspective view of the ultrasonic blade of FIG. 6 and the heat shield of FIG. 5, with the heat shield pivoted to an upward position.

When heat shield (170) is in an unlocked position, as shown in FIG. 8A, elongate body (175) may be substantially perpendicular with the longitudinal axis defined by outer sheath (132). While heat shield (170) is in the unlocked position, access is provided for cleaning portions of ultrasonic blade (152) and waveguide (154) that would otherwise be covered by heat shield (170). Additionally, tube (138) also defines an access hole (144) to provide further access to cleaning waveguide (154). When heat shield (170) is in a locked position as shown in FIG. 8B, heat shield (170) may prevent ultrasonic blade (152) from inadvertently touching non targeted tissue. Apertures (176) may allow for undesired fluid and tissue to escape the confines of heat shield (170) and ultrasonic blade (152), as to not disturb the vibration of activated ultrasonic blade (152).

As noted above, heat shield (170) includes a pair of spring locks (172). Spring locks (172) are sized to engage tube (138) when heat shield (170) pivots toward the locked position as shown in FIG. 8B. Spring locks (174) are resilient, and capable of flexing to conform to the profile of tube (138) while heat shield (170) pivots toward ultrasonic blade (152). Spring locks (172) are also dimensioned to enter locking slots (146) while heat shield (170) is in the locked position. In other words, the resilient nature of spring locks (172) allows spring locks (172) to return to their natural position once they no longer engage the profile of tube (138) by entering locking slots (146). Once spring locks (172) enter their natural position by engaging locking slots (146) of tube (138), engagement between spring locks (172) and the edges of tube (138) defining locking slots (146) maintains the rotational position of heat shield (170) relative to tube (138). Therefore, heat shield (170) may be substantially fixed relative to the rest of blade assembly (150) when heat shield (170) is in a locked position. Due to the resilient nature of spring locks (172), an operator may rotate heat shield (170) away from ultrasonic blade (152) with enough force to deflect spring locks (172) out of locking slots (146), thereby decoupling spring locks (172) from tube (138). Spring locks (172) will flex outwardly to conform to the profile of tube (138) until heat shield (170) is further pivoted to a fully unlocked position.

As best seen in FIG. 9, heat shield (170) also includes distal bumper (178). In the present example, distal bumper (178) is formed of an electrically insulative material. By way of example only, distal bumper (178) may comprise polytetrafluoroethylene (PTFE) and/or any other suitable material(s) as will be apparent to those of ordinary skill in the art in view of the teachings herein. Distal bumper (178) may be pressed into place on the distal end of heat shield (170) or attached to the distal end of heat shield (170) using any other suitable features or techniques.

When ultrasonic blade (152) is in use, ultrasonic blade (152) may deflect laterally away from the longitudinal axis in response to forces provided by contact with tissue. Such deflection may urge blade (152) into contact with heat shield (170). If heat shield (170) is made of a metallic substance and instrument (100) is configured to provide RF energy to a surgical location, as described below, a short in the circuit providing RF energy to the surgical location may occur. Distal bumper (178) may thus provide a safe contact surface for ultrasonic blade (152) to contact such that if blade (152) does deflect against the metallic material in heat shield (170) and instead just contacts distal bumper (178), a short circuit of delivered RF energy may be prevented.

C. Exemplary Rotation Detent and Tissue Stop

In some instances, clamp pad assembly (210, 410) and blade assembly (150, 550) may combine to have a proximal portion that is not capable of simultaneously severing and sealing tissue. For instance, if tissue becomes located proximal to the proximal end of clamp pad (212), and the operator closes end effector (102) on the tissue and activates blade (152), the region of tissue captured adjacent to blade (152) proximal to the proximal end of clamp pad (212) may not be compressed enough to adequately sever or seal the tissue. In some convention ultrasonic shears instruments, it may be difficult for an operator to readily determine (e.g., through visualization) whether tissue has become located in such a proximal position within end effector (102). It may therefore be desirable to provide a positive tissue stop that may prevent tissue from traveling to these proximal portions of an end effector. Such a positive tissue stop may consistently and simply prevent tissue from inadvertently reaching a proximal position within end effector (102) where ultrasonic energy from blade (152) may not adequately sever or seal the tissue. In providing such prevention, the positive tissue stop may eliminate the need for an operator to visualize proximal region of end effector (102) in order to determine whether the tissue has reached an undesirably proximal position within end effector (102). It may also be beneficial to provide tactile feedback to indicate to the operator when clamp pad assembly (210, 410) and blade assembly (150, 550) have been pivoted to angle where a positive tissue stop is no longer effective.

Figure 10A:
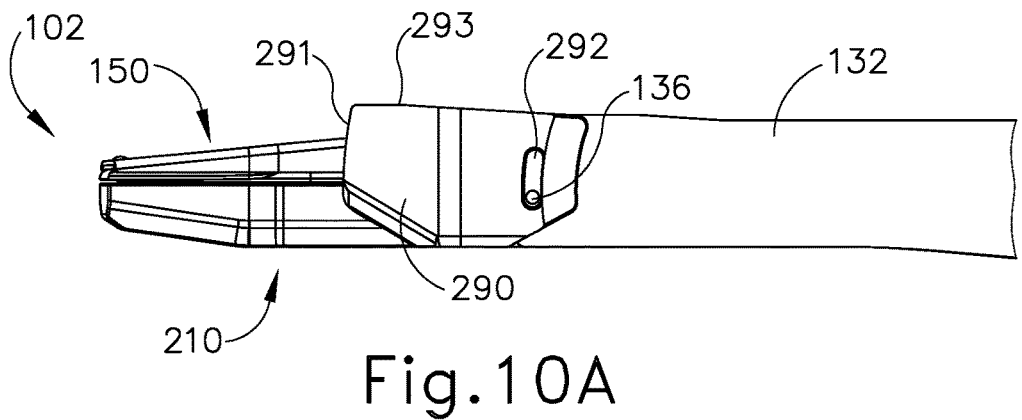
FIG. 10A depicts a side elevational view of the end effector of FIG. 1A, with the end effector in a closed configuration.
Figure 10B:
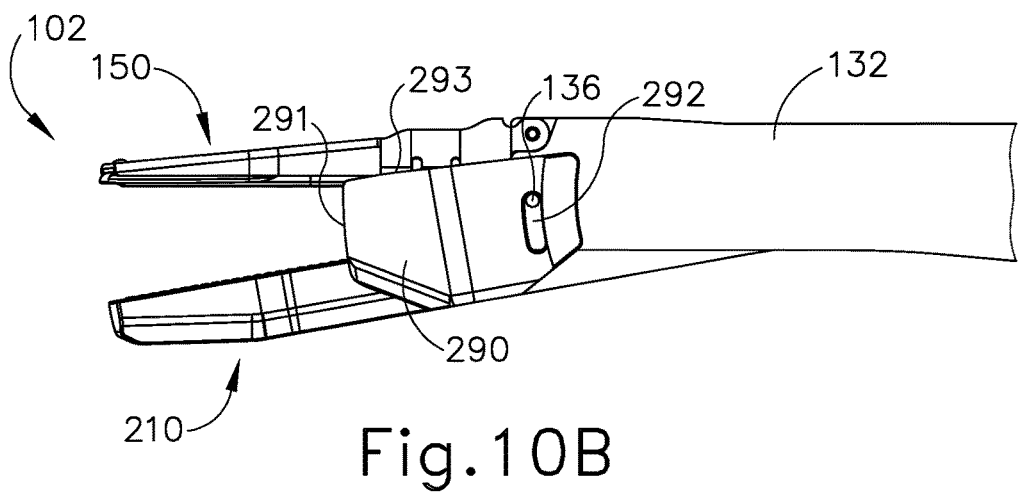
FIG. 10B depicts a side elevational view of the end effector of FIG. 1A, with the end effector in an open configuration.
Figure 10C:
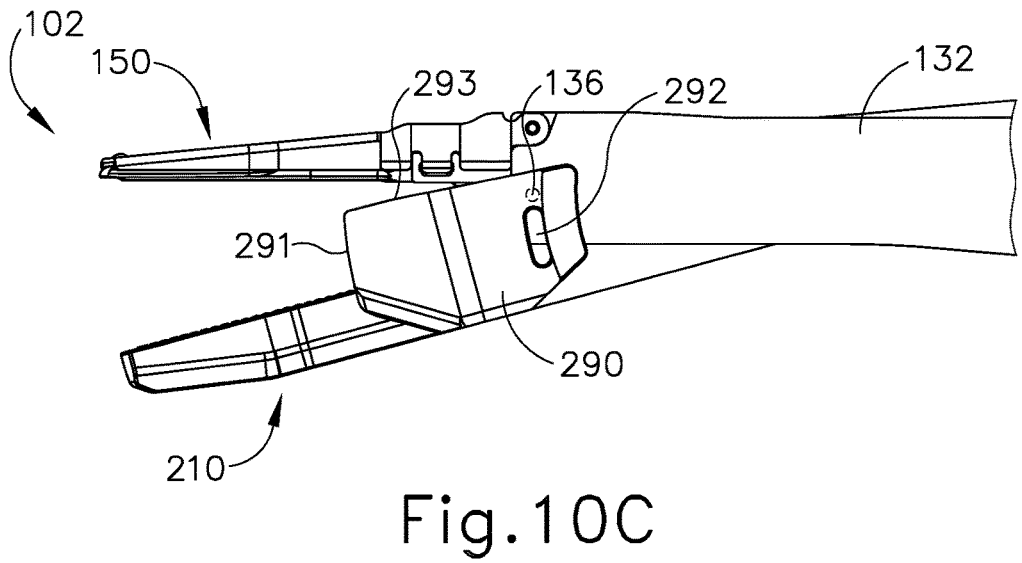
FIG. 10C depicts a side elevational view of the end effector of FIG. 1A, with the end effector in a hyperextended configuration.

FIGS. 10A-10C show clamp pad assembly (210) and blade assembly (150) with clamp pad assembly (210) pivoted at various positions relative to blade assembly (150). Clamp pad assembly (210) includes an integral tissue stop (290) defining a slot (292). Tissue stop (290) has a top surface (293) and a distally presented engagement surface (291) that is configured to contact tissue to prevent tissue from traveling proximal in relation to engagement surface (291). The longitudinal position of engagement surface (291) is located just distal to the longitudinal position of the proximal end of clamp pad (212). Thus, the portions of clamp pad assembly (210) and blade assembly (150) that are proximal to engagement surface (291) may not be able to sufficiently sever and seal tissue as described above. Therefore, if tissue were captured between the portions of clamp pad assembly (210) and blade assembly (150) that are proximal in relation to engagement surface (291), the operator may mistakenly believe that the tissue has been sufficiently severed and sealed, when in fact it has not. Engagement surface (291) of tissue stop (291) thus prevents tissue from traveling to this portion of end effector (202).

Tissue stop may be effective so long as top surface (293) is above or level with the tissue engagement region of blade assembly (150), as shown in FIGS. 10A-10B. However, as shown in FIG. 10C, if top surface (293) is below the tissue engagement region of blade assembly (150), tissue may be captured between the portion of clamp pad assembly (210) and blade assembly (150) that is proximal to engagement surface (291). A lower locating pin (136) projects laterally outwardly from outer sheath (132). Lower locating pin (136) is located within an arcuate slot (292) defined by tissue stop (290). Lower locating pin (136) protrudes within slot (292) to act as a detent in such a way that when top surface (293) is no longer above or level with the tissue engagement region of blade assembly (150), pin (136) engages the end of slot (292) and then exits slot (292), thereby providing tactile feedback indicating that end effector (102) has been opened beyond the configuration shown in FIG. 10B. Therefore, the operator may readily discern when the operator has opened clamp pad assembly (210) to an angle in relation to blade assembly (150) where top surface (293) is no longer above or level with the tissue engagement region of blade assembly (150).

II. EXEMPLARY ALTERNATIVE SURGICAL INSTRUMENT

A. Overview

Figure 11A:
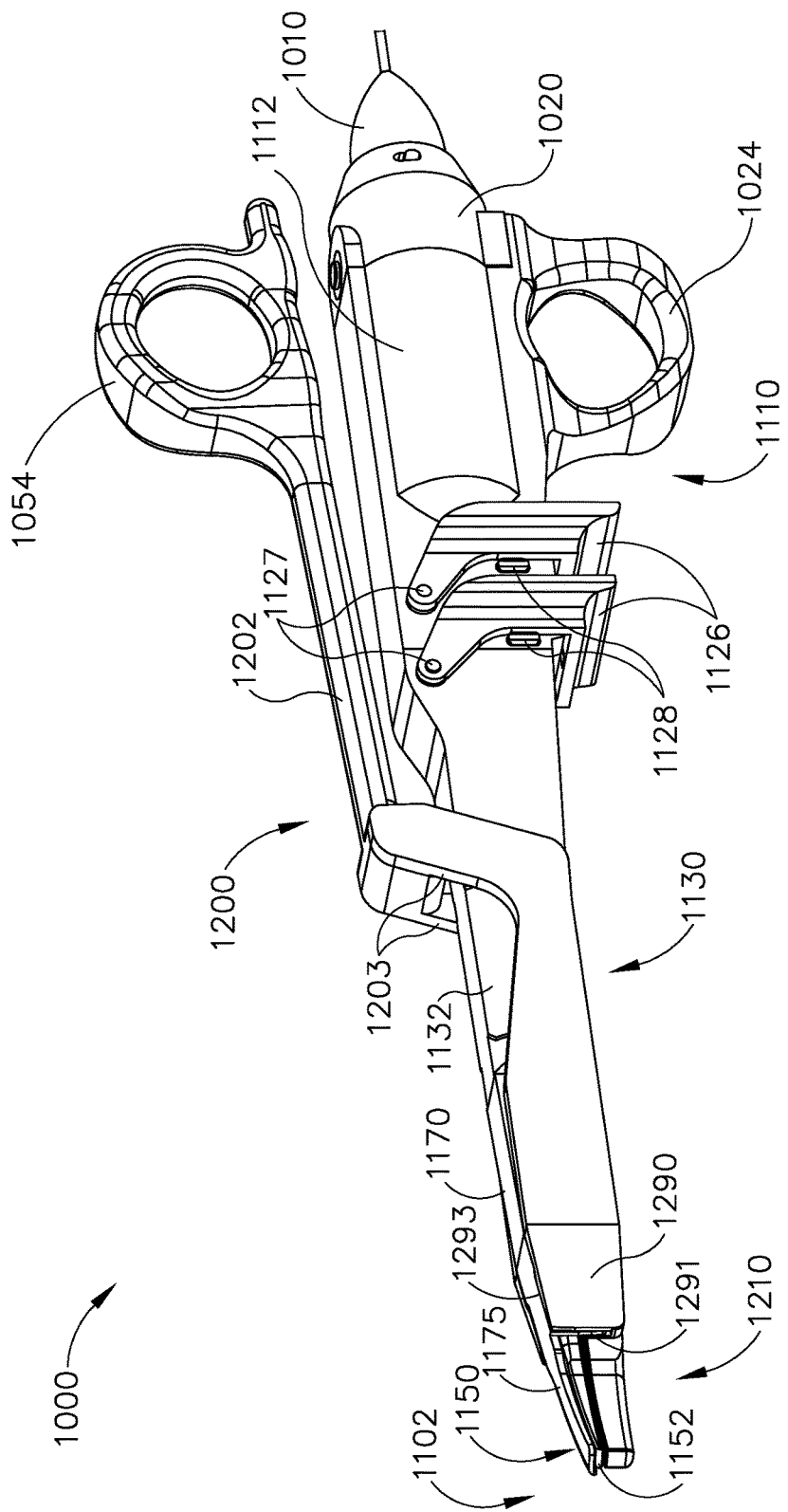
FIG. 11A depicts a perspective view of an exemplary alternative surgical instrument, with an end effector in a closed configuration.
Figure 11B:
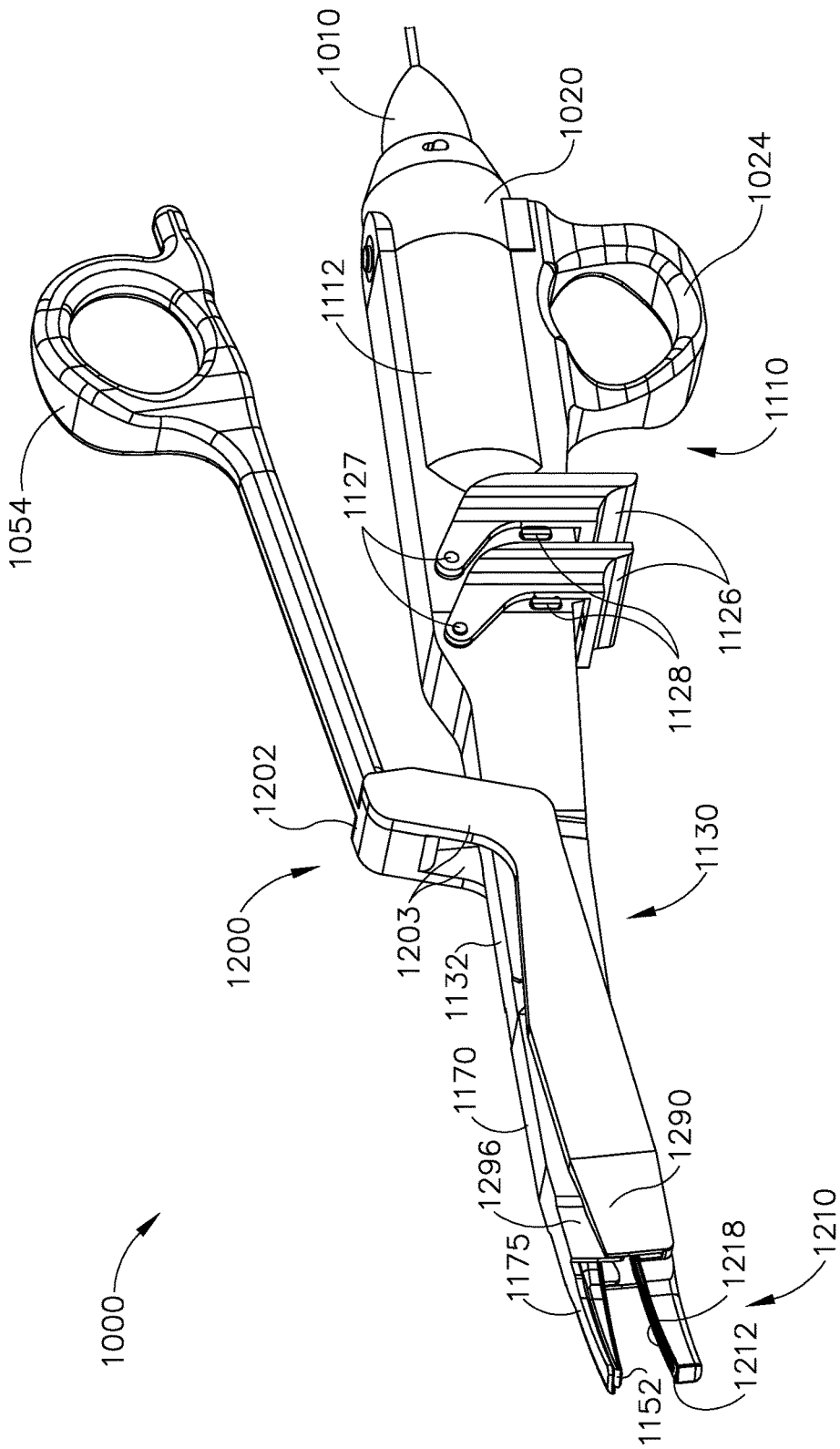
FIG. 11B depicts a perspective view of the instrument of FIG. 11A, with the end effector in an open configuration.

FIGS. 11A-11B show an alternative instrument (1000) with a clamp arm assembly that is detachable from a shaft assembly. Instrument (1000) is substantially similar to instrument (100) described above, except for the differences noted below. Therefore, instrument (1000) may be capable of delivering both ultrasonic energy and radio frequency (RF) energy to a surgical site.

Instrument (1000) of this example comprises a plug (1010), a proximal casing (1020), handle assembly (1110), a shaft assembly (1130), a blade assembly (1150), a clamp arm assembly (1200), and an end effector (1102). As will be described in greater detail below, clamp arm assembly (1200) may be selectively attached to handle assembly (1110) and detached from handle assembly (1110). The ability to selectively attach and detach clamp arm assembly (1200) from handle assembly (1110) may provide additional benefits of reusability for either handle assembly (1110) or clamp arm assembly (1200).

Handle assembly (1110) comprises a body (1112) including a finger grip ring (1024) and a pair of buttons (1126). Clamp arm assembly (1200) partially pivots toward and away from body (1112) of handle assembly (1110). Clamp arm assembly (1200) includes a body (1202) with a thumb grip ring (1054). Thumb grip ring (1054) and finger grip ring (1024) together provide a scissor grip type of configuration. It should be understood, however, that various other suitable configurations may be used, including but not limited to a pistol grip configuration.

Figure 12:
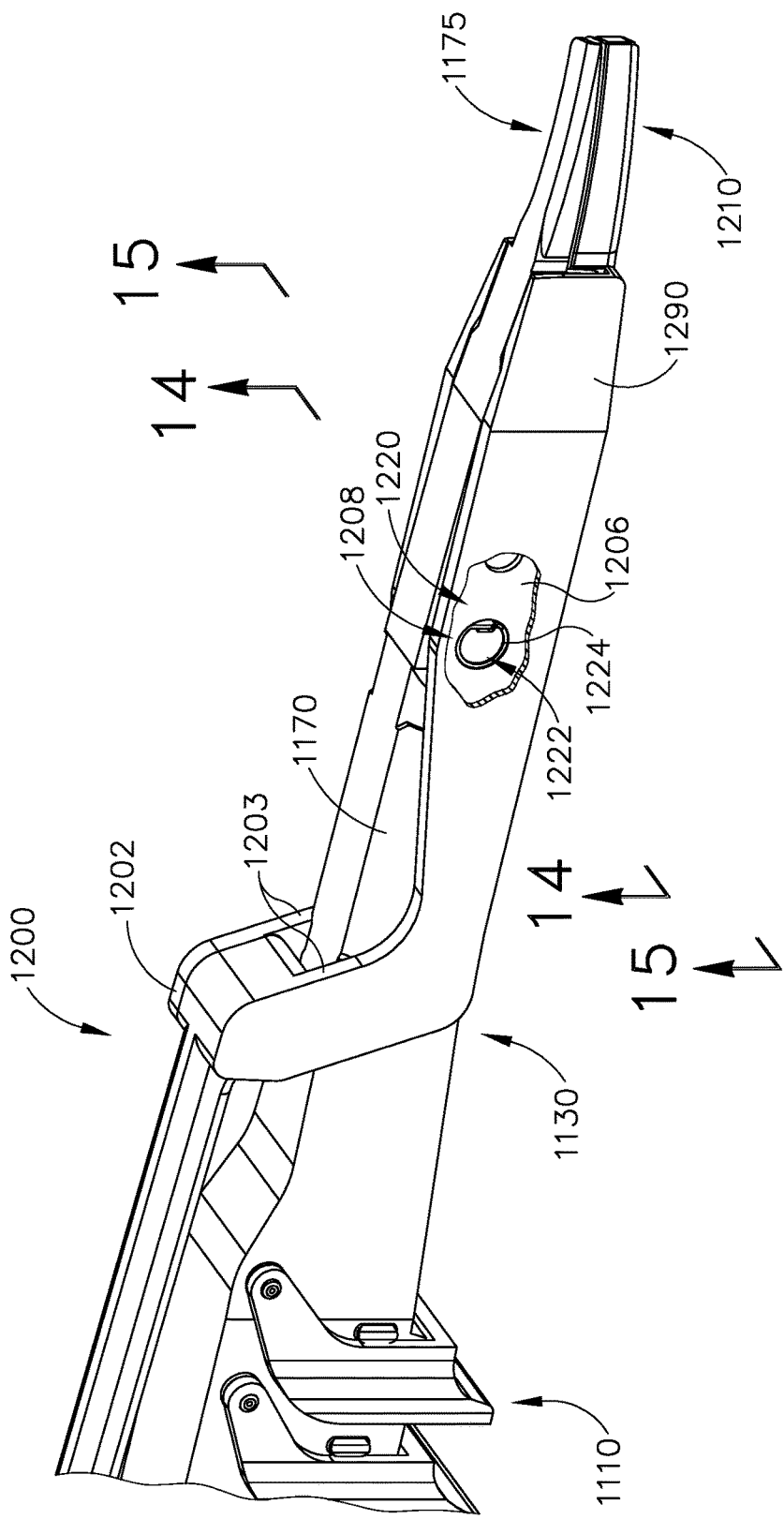
FIG. 12 depicts a partial perspective view of a distal portion of the instrument of FIG. 11A, with a portion of the clamp arm broken away to reveal a coupling assembly.

Shaft assembly (1130) comprises an outer sheath (1132) extending distally from body (1112). As will be described in greater detail below, outer sheath (1132) includes electrical traces and/or other electrically conductive features. As best seen in FIGS. 11A-12, end effector (1102) comprises an ultrasonic blade (1152) and a clamp pad assembly (1210). Ultrasonic blade (1152) extends distally from outer sheath (1132). Similar to instrument (100) described above, ultrasonic blade (1152) is a part of blade assembly (1150). Clamp arm assembly (1200) includes a pivotable member (1170) that is pivotally coupled to a Y-portion (1203) of body (1202) via a pair of bosses (1172) housed within a pair of complementary recess (1205) of Y-portion (1203).

Clamp pad assembly (1210) is an integral feature of body (1202) of clamp arm assembly (1200). More specifically, clamp pad assembly (1210) is fixed to Y-portion (1203) of body (1202). Therefore, clamp pad assembly (1210) may pivot relative to pivotable member (1170). Clamp pad assembly (1210) includes a clamp pad (1212) facing ultrasonic blade (1152) and an electrode (1218). As will be described in greater detail below, pivotable member (1170) is configured to receive blade assembly (1150) and a portion of shaft assembly (1130) via channel (1171). Clamp pad assembly (1210) is positioned distally in relation to complementary recess (1204); while body (1202) and thumb grip ring (1154) are positioned proximal to complementary recess (1202). Thus, as shown in FIGS. 11A-11B, clamp pad assembly (1210) is pivotable toward and away from both pivotable member (1170) and ultrasonic blade (1152) based on pivoting of thumb grip ring (1054) toward and away from body (1112) of handle assembly (1110). It should therefore be understood that an operator may squeeze thumb grip ring (1054) toward body (1112) to thereby clamp tissue between clamp pad assembly (1210) and ultrasonic blade (1152) to transect and/or seal the tissue using ultrasonic energy and/or RF energy. In some versions, one or more resilient members are used to bias clamp pad assembly (1210) to the open position shown in FIG. 35B. By way of example only, such a resilient member may comprise a leaf spring, a torsion spring, and/or any other suitable kind of resilient member.

B. Exemplary Electrical Coupling Assembly

FIGS. 12-15 show an exemplary electrical coupling assembly (1220) that may be readily incorporated into instrument (1000). As can be seen in FIG. 12, electrical coupling assembly (1220) is incorporated into clamp arm assembly (1200) of instrument (1000) to provide electrical communication of RF energy between handle assembly (1110) and coupling assembly (1220).

Figure 13:
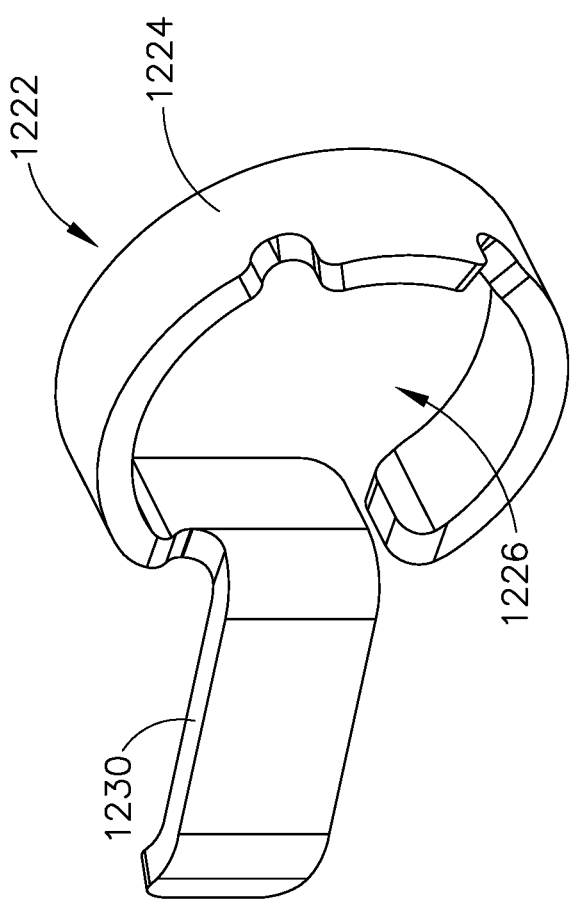
FIG. 13 depicts a perspective view of an exemplary conducting member of the coupling assembly of FIG. 12.

Coupling assembly (1220) comprises a conducting member (1222) that is insertable into a coupling opening (1208) of inner core (1202) of clamp arm assembly (1200). As best seen in FIG. 13, conducting member (1222) comprises a receiving portion (1224) and a contact portion (1230). Conducting member (1222) generally comprises a material having both electrically conductive and resilient properties. In some examples, conducting member (1222) comprises an electrically conductive metal such as copper, gold, steel, aluminum, silver, etc. In still other examples, conducting member (1222) comprises an electrically conductive non-metallic material such as conducting polymers, silicides, graphite, etc.

Receiving portion (1224) of conducting member (1222) generally comprises a strip with a rectangular cross-section formed in a partial ring. Although receiving portion (1224) of the present example is shown as only defining a partial ring shape (e.g., breaking adjacent to contact portion (1230)), it should be understood that in other examples receiving portion (1224) forms a complete ring. The ring shape of receiving portion (1224) defines a central opening (1226). As will be described in greater detail below, opening (1226) is configured to receive boss (1172).

Receiving portion (1224) is configured to fit within coupling opening (1208) of inner core (1202). As will be described in greater detail below, receiving portion (1224) is generally held in position by the interface between inner core (1202) and boss (1172). In addition, or in alternative, receiving portion (1224) may be held in position by other suitable means. For instance, in some examples receiving portion (1224) is welded in position or otherwise fastened to inner core (1202). Regardless of how receiving portion (1224) is secured within coupling opening (1208), it should be understood that receiving portion (1224) is generally configured to provide a mechanical ground for contact portion (1230), as will be described in greater detail below.

Figure 14:
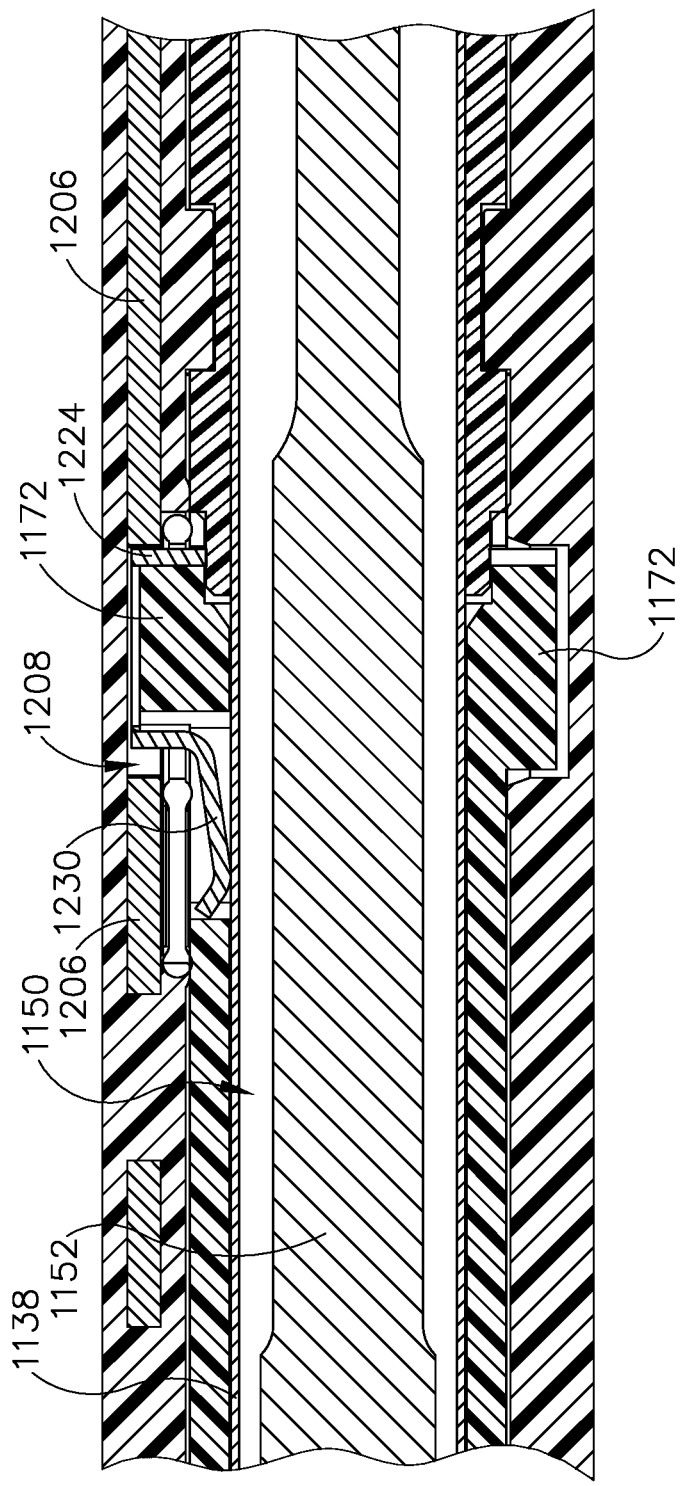
FIG. 14 depicts a cross-sectional view of the instrument of FIG. 11A, taken along line 14-14 of FIG. 12.

Contact portion (1230) extends laterally and outwardly away from the outer diameter defined by receiving portion (1224). In particular, contact portion (1230) is shaped to form a resilient brush or contact. It should be understood that the term "resilient" used herein with respect to contact portion (1230) is used to refer to a rigid yet deformable character of contact portion (1230). For instance, contact portion (1230) is generally biased toward the position shown in FIG. 14. However, through engagement with various components of handle assembly (1110), contact portion (1230) may elastically deform in response to such engagement. After such engagement is removed, contact portion (1230) may return to its original configuration as shown in FIG. 14. As will be described in greater detail below, this shape permits contact portion (1230) to engage at least a portion of handle assembly (1110) to provide electrical communication between clamp arm assembly (1200) and handle assembly (1110).

As is best seen in FIG. 14, when conducting member (1222) is disposed within clamp arm assembly (1200) and clamp arm assembly (1200) is attached to handle assembly (1110) as described above, contact portion (1230) of conducting member (1222) extends transversely into handle assembly (1110). Inside handle assembly (1110), contact portion (1230) engages outer sheath (1132) of shaft assembly (1130). When contact portion (1230) is engaged with outer sheath (1132), contact portion (1230) deforms against outer sheath (1132) to provide electrical continuity between contact portion (1230) and outer sheath (1132). When in use, conducting member (1222) may rotate relative to boss (1172) as clamp arm assembly (1200) is pivoted. Because of the deformation and resilient character of contact portion (1230), it should be understood that even if conducting member (1222) engages in some rotation, contact portion (1230) will continue to bear against outer sheath (1132), thereby maintaining electrical continuity between contact portion (1230) and outer sheath (1132).

As described above, receiving portion (1224) is disposed within coupling opening (1208) of inner core (1202). Receiving portion (1224) is held in position between inner core (1202) and boss (1172). This generally secures receiving portion (1224) relative to inner core (1202) but may still permit some relative rotation between boss (1172) or inner core (1202). Receiving portion (1224) is generally secured to inner core (1204) to provide a mechanical ground such that receiving portion (1224) remains fixed while contact portion (1230) resiliently bears against outer sheath (1132). Additionally, receiving portion (1224) is in physical contact with inner core (1202). Because both inner core (1224) and receiving portion (1224) comprise electrical conductors, it should be understood that such physical contact between receiving portion (1224) and inner core (1204) provides electrical continuity between inner core (1204) and conducting member (1222).

Figure 15:
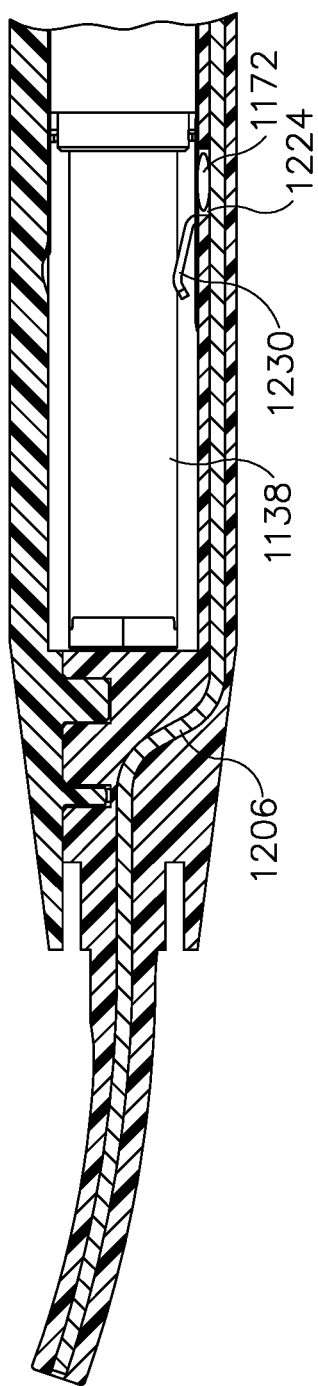
FIG. 15 depicts a cross-sectional view of the instrument of FIG. 11A, taken along line 15-15 of FIG. 12.

FIG. 15 shows an exemplary current path for coupling assembly (1220). As can be seen, structural core (1204) of body (1202) extends through body (1202) to the distal end of body (1202). Although not shown, it should be understood that at the distal end of body (1202) structural core (1204) is coupled to electrode (1218) as described above. Thus, structural core (1204) is configured to be in electrical communication with electrode (1218).

As described above, conducting member (1222) of coupling assembly (1220) is secured to body (1202) to be in electrical communication with structural core (1204). Thus, conducting member (1222) is configured to be in electrical communication with electrode (1218) via structural core (1204). As also described above, outer sheath (1132) of shaft assembly (1130) is also in electrical communication with conducting member (1222) via contact portion (1230). Thus, the engagement between contact portion (1230) and outer sheath (1132) also provides an electrical coupling between clamp arm assembly (1200) and handle assembly (1110). Because conducting member (1222) is configured to be in electrical communication with electrode (1218), the electrical coupling between outer sheath (1132) and contact portion (1230) is configured to permit electrical communication between handle assembly (1110) and electrode (1218). Outer sheath (1132) of handle assembly (1110) is then in electrical communication with generator (5). Thus, coupling assembly (1220) provides a current path from generator (5) to electrode so that an RF energy circuit may be formed with blade (152) and electrode (1218) when end effector (1102) is used to grasp tissue.

C. Exemplary Assembly

As mentioned above, clamp arm assembly (1200) may be selectively attached to handle assembly (1110) and detached from handle assembly (1110). FIGS. 16A-17D show clamp arm assembly (1200) coupling with handle assembly (1110). Unlike the examples described above, where a clamp arm assembly couples with handle assembly by moving along a path that is transverse to the longitudinal axis of the handle assembly, clamp arm assembly (1200) of the present example couples with handle assembly (1110) by moving along a path that is aligned with the longitudinal axis of handle assembly (1100).

Figure 16A:
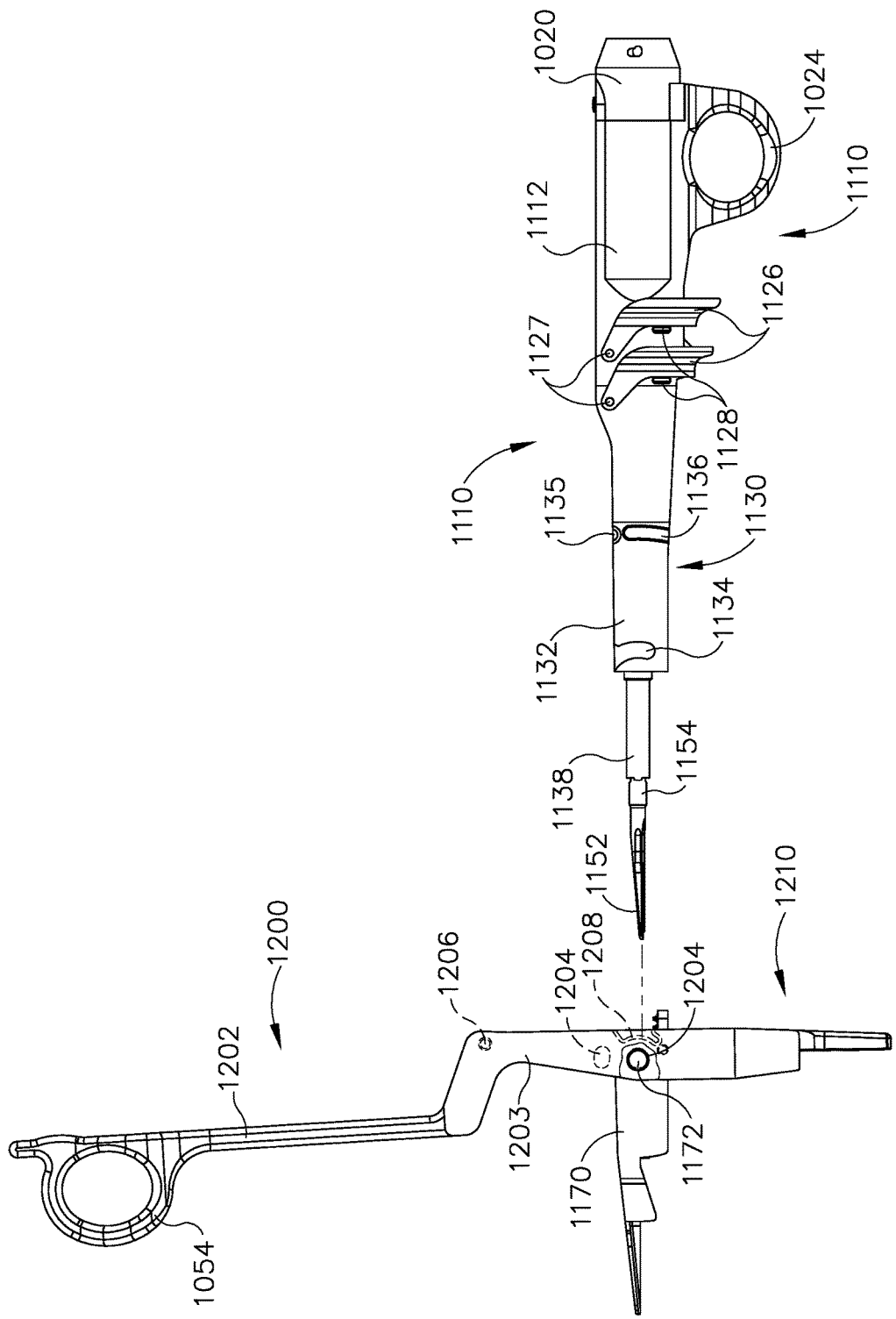
FIG. 16A depicts a side elevational view of the instrument of FIG. 11A, with a clamp arm assembly separated from a handle assembly.
Figure 16B:
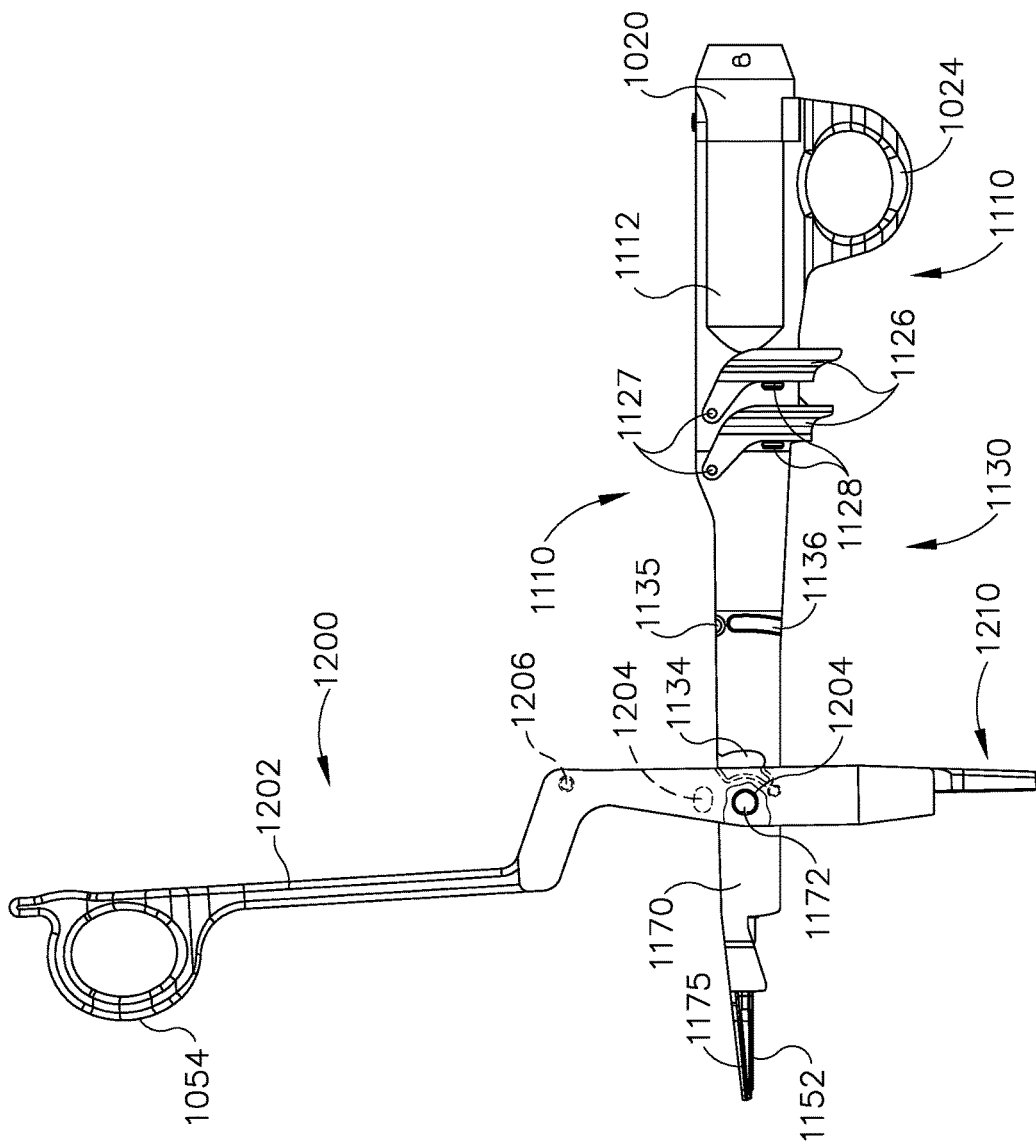
FIG. 16B depicts a side elevational view of the instrument of FIG. 11A, with the clamp arm assembly coupled with handle assembly, and with a clamp arm of the clamp arm assembly in a first pivotal position in relation to the handle assembly.
Figure 16C:
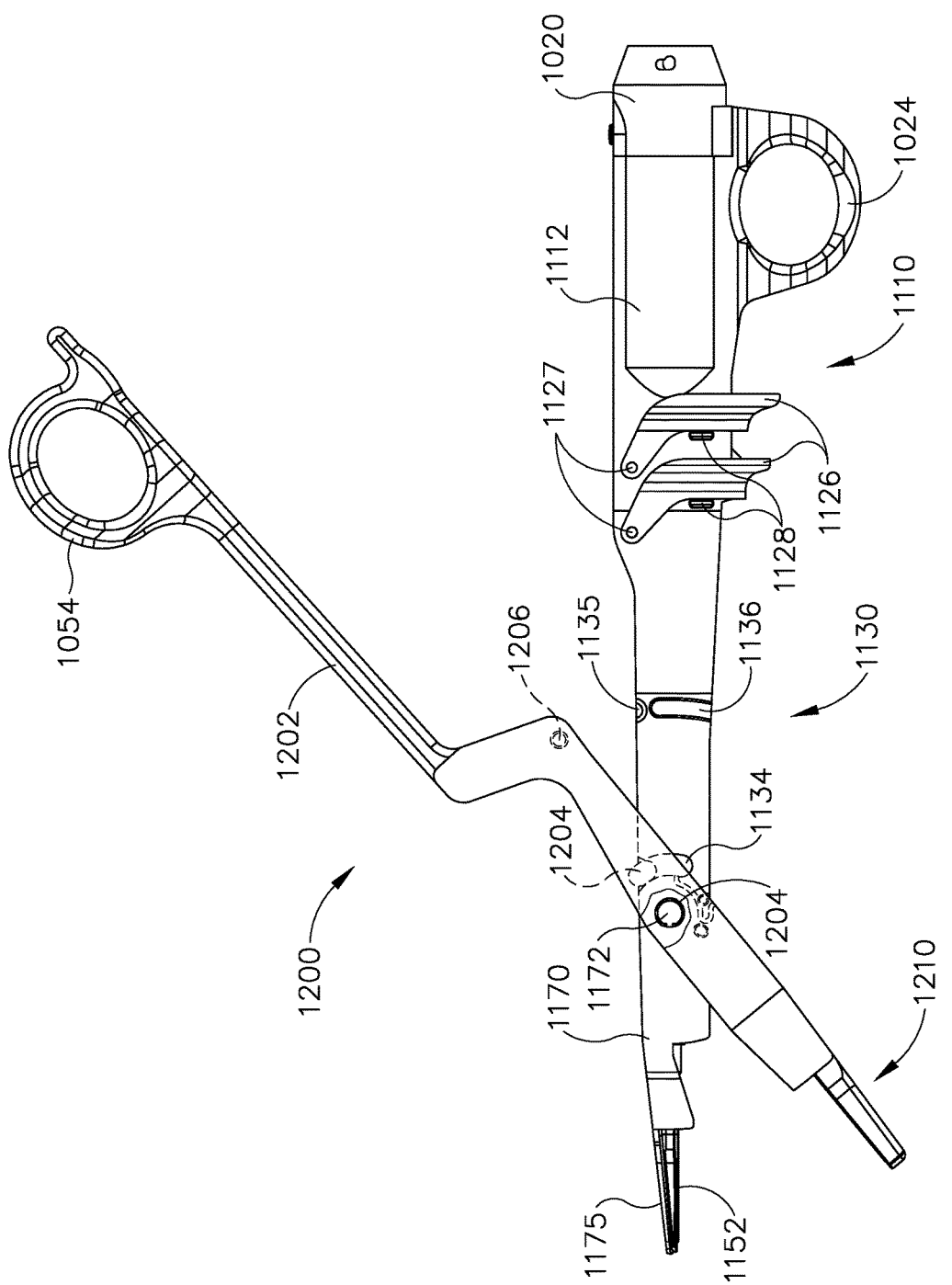
FIG. 16C depicts a side elevational view of the instrument of FIG. 11A, with the clamp arm assembly coupled with handle assembly, and with the clamp arm in a second pivotal position in relation to the handle assembly.
Figure 16D:
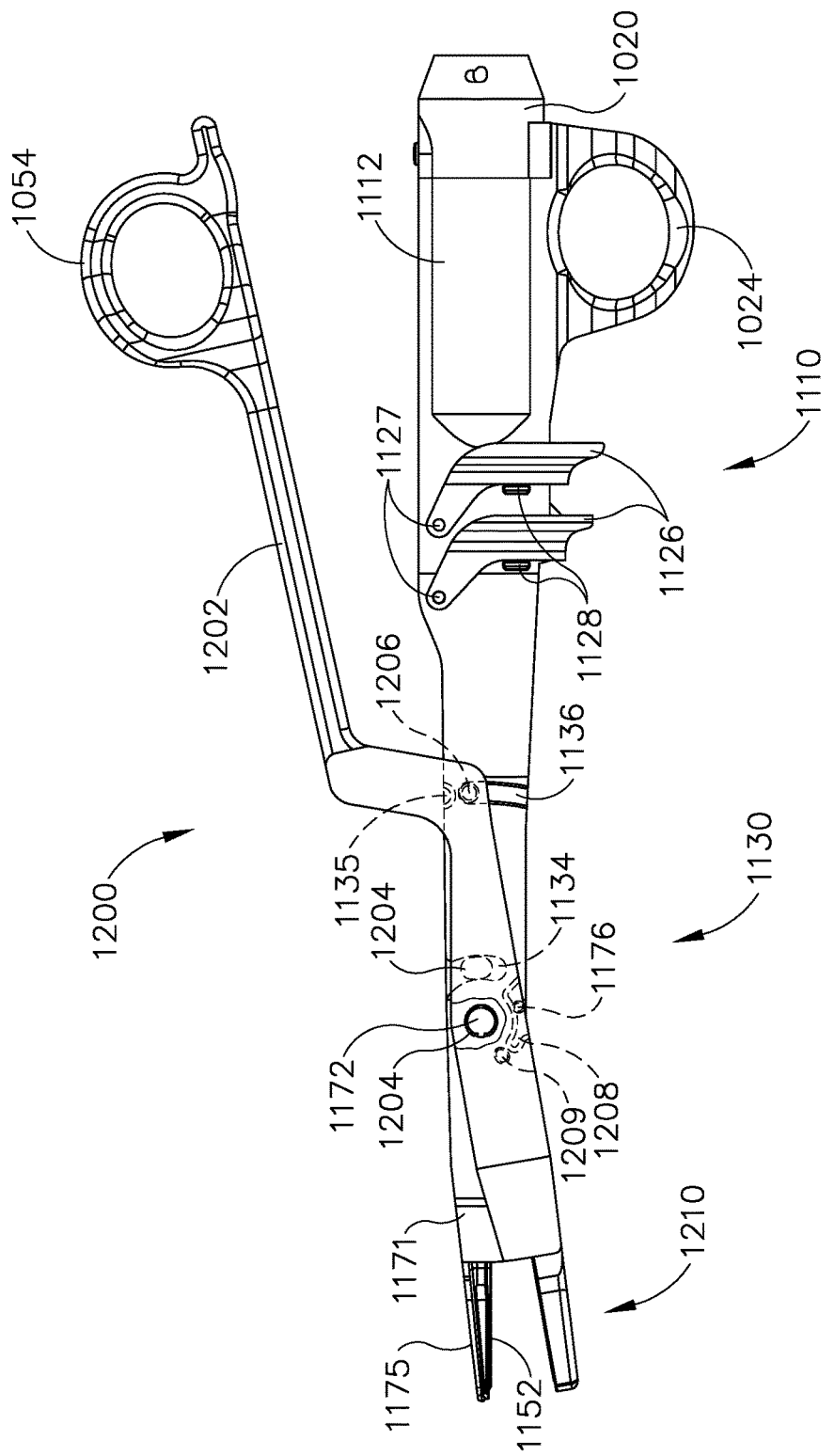
FIG. 16D depicts a side elevational view of the instrument of FIG. 11A, with the clamp arm assembly coupled with handle assembly, and with the clamp arm in a third pivotal position in relation to the handle assembly.
Figure 17A:
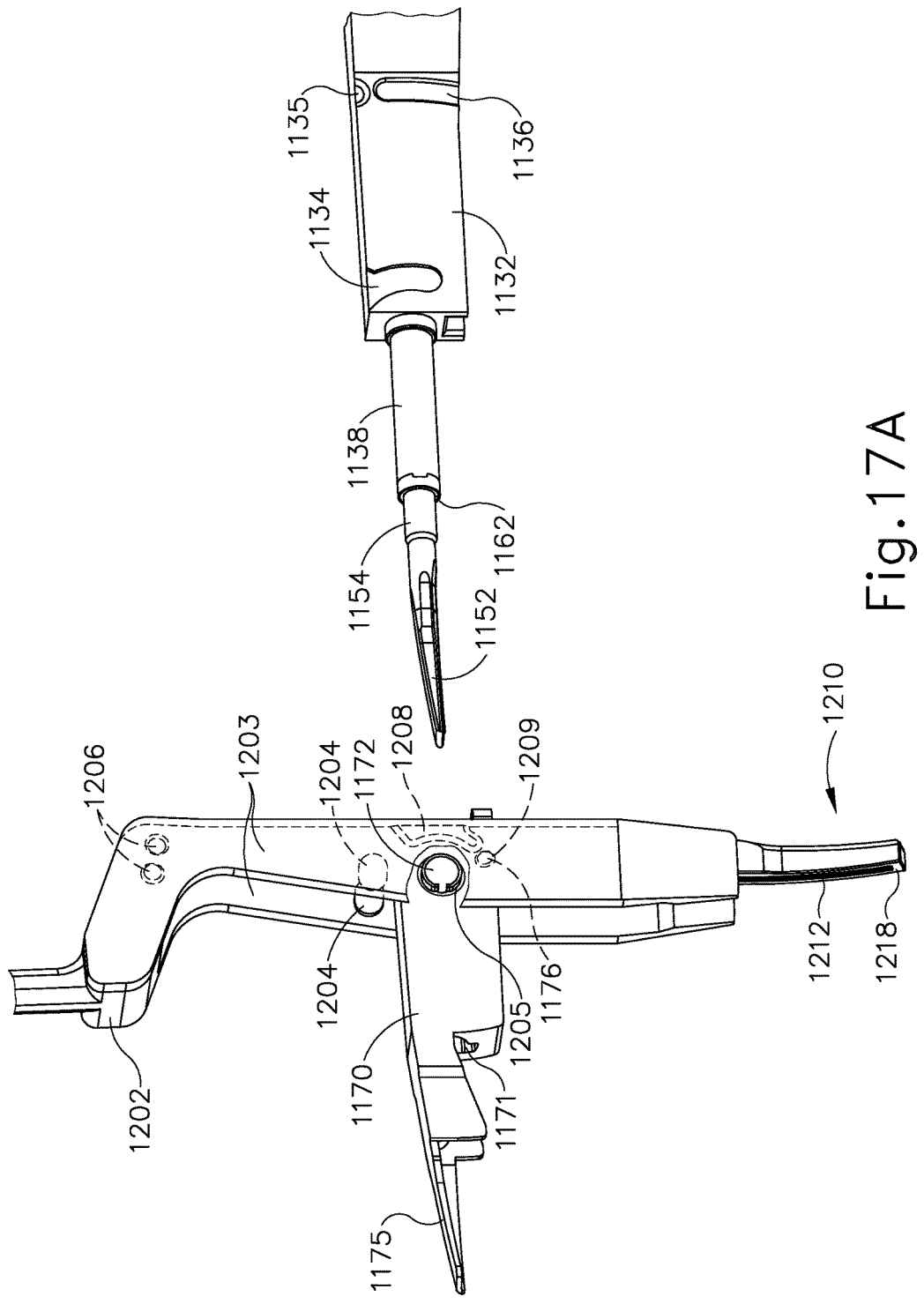
FIG. 17A depicts a perspective view of the instrument of FIG. 11A, with the clamp arm assembly separated from the handle assembly.
Figure 17B:
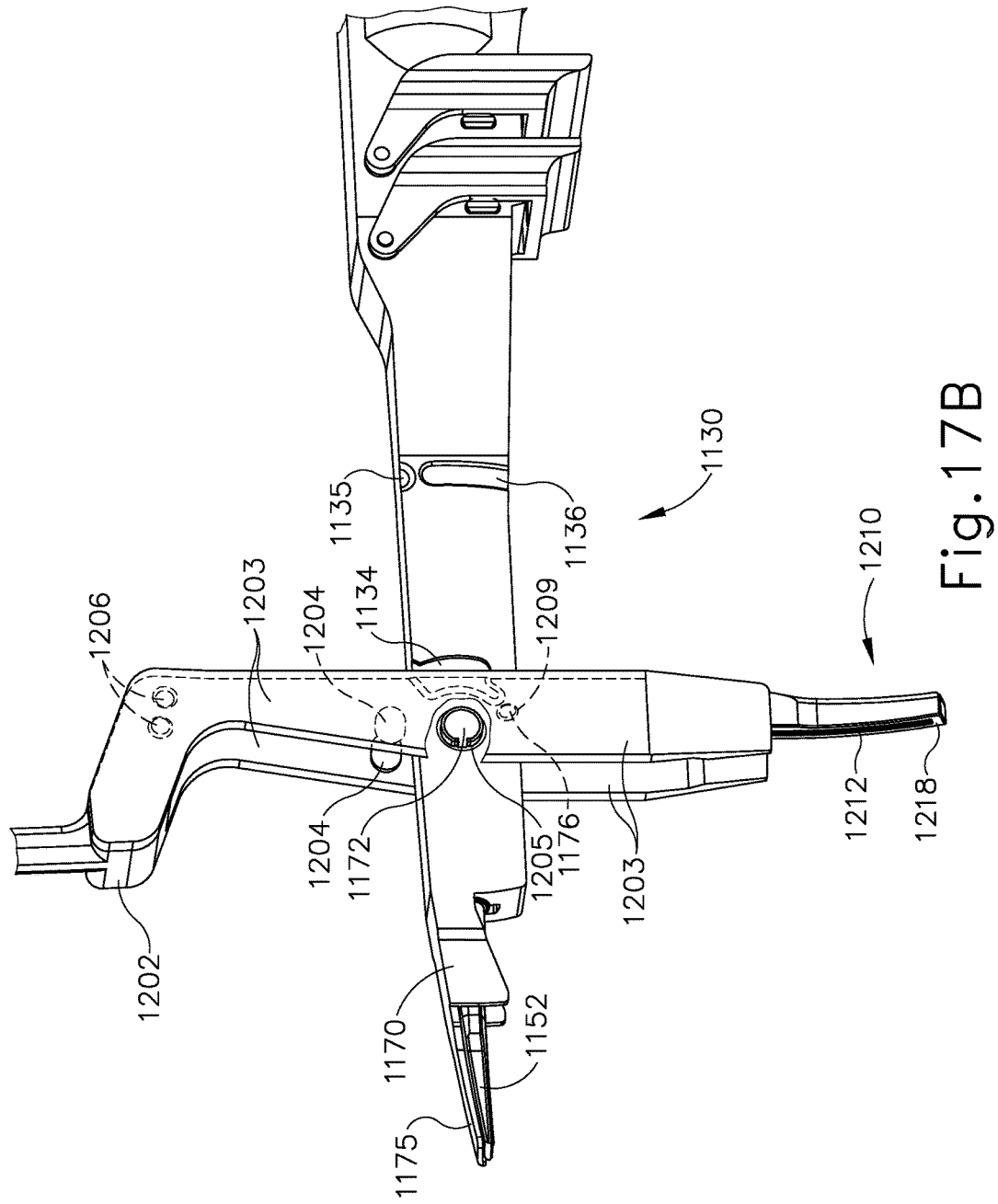
FIG. 17B depicts a perspective view of the instrument of FIG. 11A, with the clamp arm assembly coupled with handle assembly, and with a clamp arm of the clamp arm assembly in the first pivotal position in relation to the handle assembly.
Figure 17C:
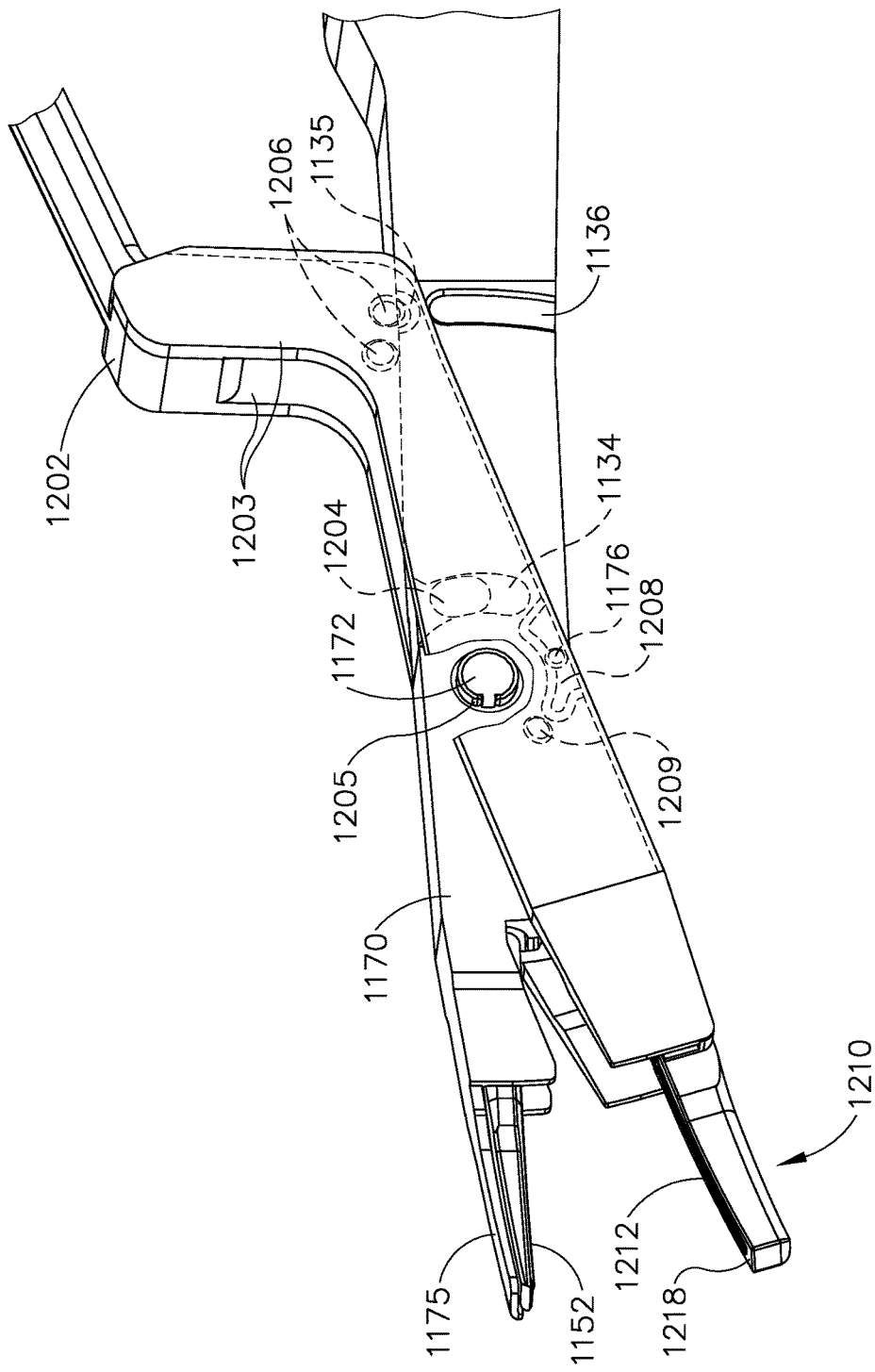
FIG. 17C depicts a perspective view of the instrument of FIG. 11A, with the clamp arm assembly coupled with handle assembly, and with a clamp arm of the clamp arm assembly in an intermediate pivotal position that is between the second pivotal position and the third pivotal position in relation to the handle assembly.
Figure 17D:
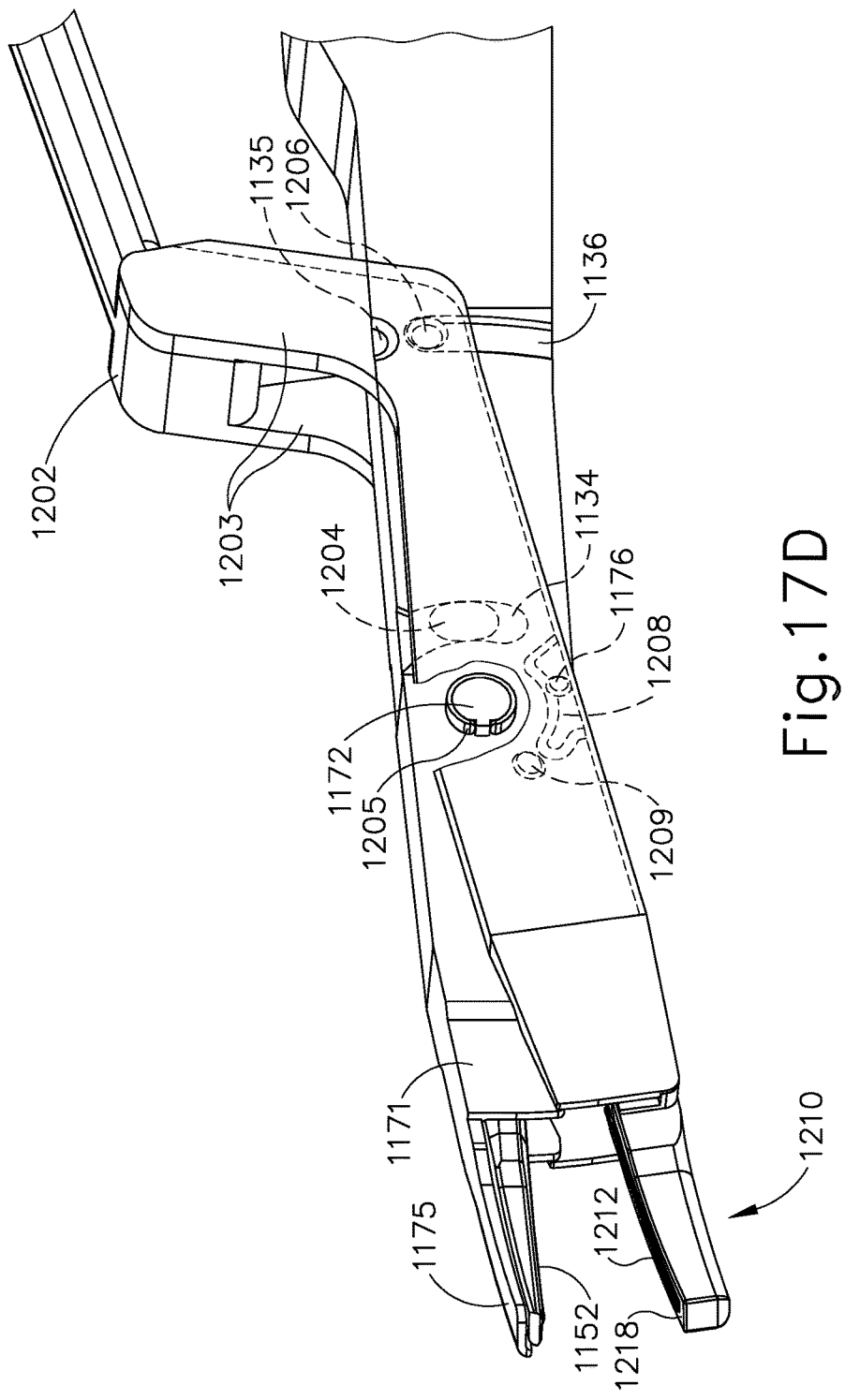
FIG. 17D depicts a perspective view of the instrument of FIG. 11A, with the clamp arm assembly coupled with handle assembly, and with a clamp arm of the clamp arm assembly in the third pivotal position in relation to the handle assembly.

FIGS. 16A and 17A show clamp arm assembly (1200) decoupled from handle assembly (1110). At this point, pivotable member (1170) is pivoted to be substantially perpendicular with body (1202). Pivotable member (1170) includes detents (1176) that are positioned to rest within recesses (1209) located on the inner surface of Y-portion (1203) when pivotable member (1170) is substantially perpendicular with body (1202). Detents (1176) and recesses (1209) provide a snap fit relationship with each other. Therefore, when detents (1176) are within recesses (1209), detents (1176) and recesses (1209) interact to provide a frictional braking force. This fictional breaking force may help prevent pivotable member (1170) from rotating relative to body (1202); thereby assisting pivotable member (1170) in retaining a perpendicular relationship with body (1202). Detents (1176) are dimensioned such that without recesses (1209), detents would have an interference fit with the inside surfaces of Y-portion (1203). Maintaining a perpendicular relationship between pivotable member (1170) and body (1202) may allow for easier insertion of handle assembly (1110) into channel (1171) of pivotable member (1170). The frictional braking force provided by detents (1176) positioned in recesses (1209) may be overcome by hand. Therefore, once handle assembly is positioned within channel (1171), an operator may rotate body (1202) toward handle assembly (1110) to force detents (1176) to snap out of recesses (1209), as shown in FIGS. 16B-16C and FIGS. 17B-17C.

The inner surface of Y-portion (1203) includes another pair of arcuate recesses (1208) dimensioned to receive detents (1176). As mentioned above, detents (1176) are dimensioned to have an interference with the inside surfaces of Y-portion (1203). Recesses (1208) are dimensioned to allow detents (1176) to travel within recesses (1208) while body (1202) rotate towards and away from handle assembly (1110), without providing any frictional braking force due to the interference fit between inside surfaces of Y-portion (1203) and detents (1176). This relationship between recesses (1208) and detents (1176) may allow the operator to possess greater rotational control between clamp arm assembly (1200) and handle assembly (1110), as shown in FIGS. 16C-16E and FIGS. 17C-17D.

Figure 16E:
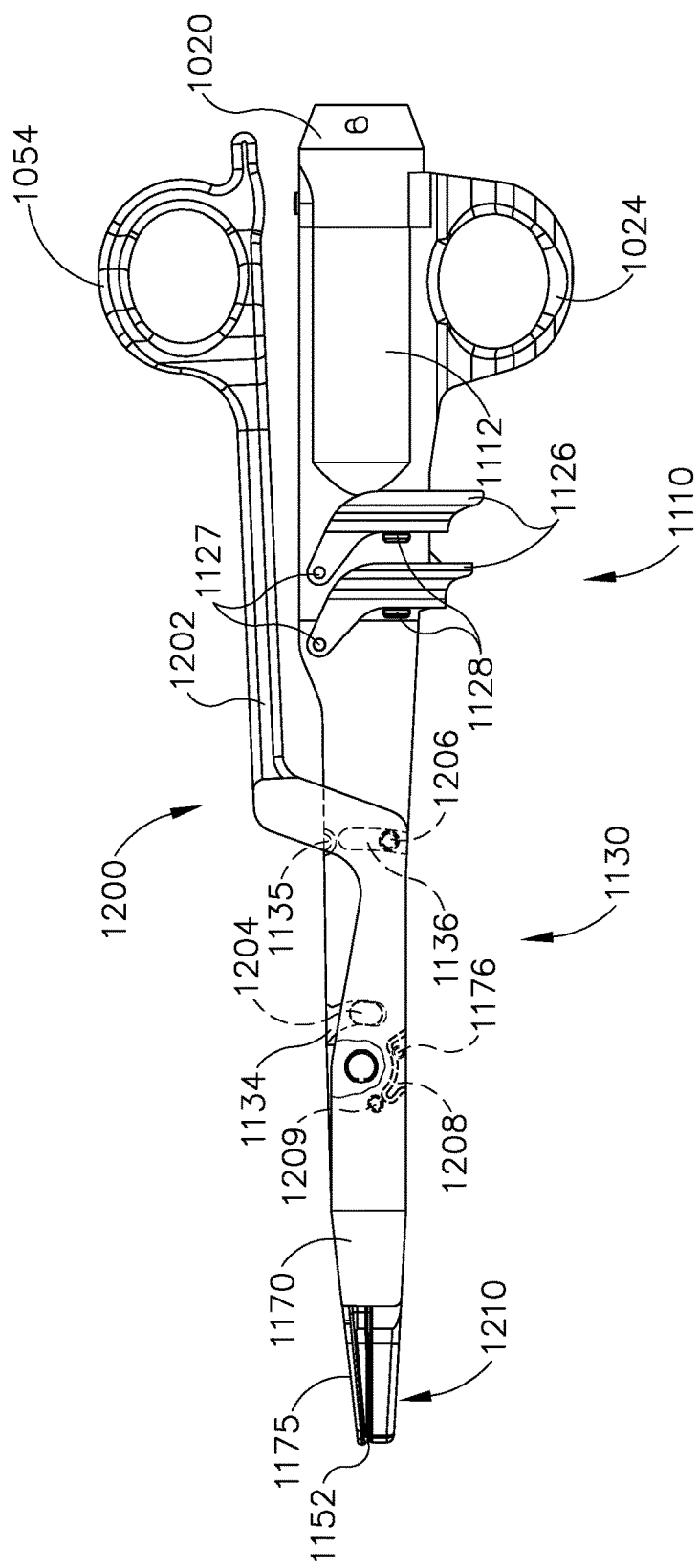
FIG. 16E depicts a side elevational view of the instrument of FIG. 11A, with the clamp arm assembly coupled with handle assembly, and with the clamp arm in a fourth pivotal position in relation to the handle assembly.

Y-portion (1203) of handle assembly (1200) also includes a pair of protrusions (1204) positioned along Y-portion (1203) to enter arcuate channels (1134) of shaft assembly (1130) when handle assembly (1200) rotates towards shaft assembly (1130). As shown in FIGS. 16C-16D and FIGS. 17C-17D, once protrusions (1204) enter channels (1134), shaft assembly (1130) and clamp arm assembly (1200) may no longer translate relative to each other. In other words, the protrusions (1204) and channels (1134) interact with each other to act as a longitudinal locking mechanism for instrument (1000). Additionally, channels (1134) define a path of angular rotation in which clamp arm assembly (1200) may rotate relative to handle assembly (1110). In the case at hand, as shown in FIG. 16E, channels (1134) are long enough to allow clamp pad assembly (1210) to close against blade (1152).

Y-portion (1203) also includes an additional pair of detents (1206) that are positioned to mate with indicating recesses (1135) and arcuate angle channels (1136). Detents (1206) are designed to slide within angle channel (1136)

while clamp pad assembly (1201) rotates relative to blade (1152) at a predetermined range of angles. When clamp arm assembly (1200) rotates toward handle assembly (1110), detents (1206) provide tactile feedback when transitioning from indicating recesses (1135) to angle channels (1136). This tactile feedback indicates to the operator that clamp arm assembly (1200) is how sufficiently coupled to handle shaft assembly (1130) and ready for use.

During operation, clamp pad assembly (1210) may rotate to an angle where detents (1206) snap out of angle channels (1136) and into indicating recesses (1135). This may provide tactile feedback to an operator indicating that clamp pad assembly (1210) has rotated past the predetermined rage of operating angles defined by angle channels (1136). This feedback may indicate to the operator user that clamp pad assembly (1201) is at an angle relative to blade (1152) beyond the predetermined range of operating angles.

D. Exemplary Heat shield and Tissue Stop

Figure 18:
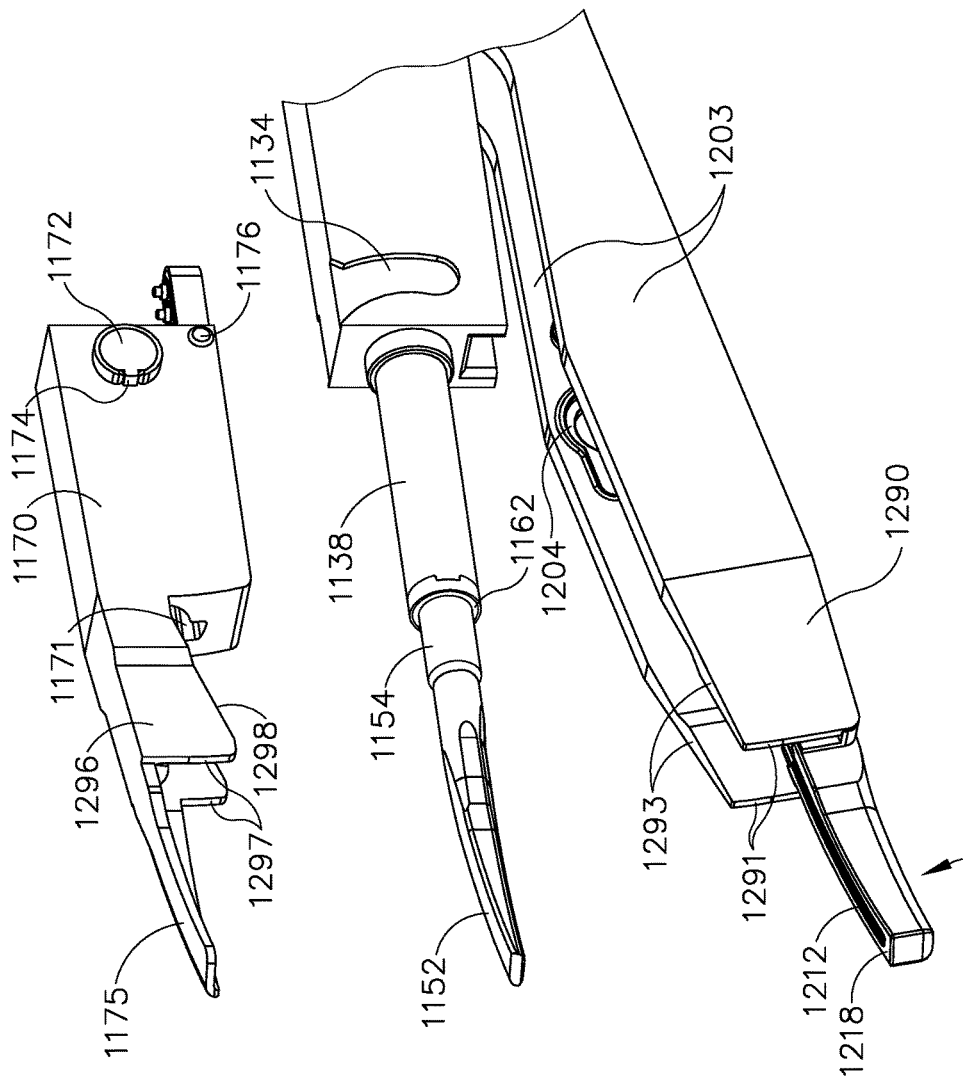
FIG. 18 depicts an exploded perspective view of the end effector of the instrument of FIG. 11A.

As mentioned above, in some instances, end effector (1102) may have a proximal portion that is not capable of sufficiently severing and sealing tissue. In such instances, it may be beneficial to provide for a tissue stop that may prevent tissue from traveling to these proximal portions of an end effector. As seen in FIG. 18, Y-portion (1203) comprises a first tissue stop (1290) while pivotable member (1170) comprises a second tissue stop (1296). Unlike tissue stop (291) described above, first tissue stop (1290) and second tissue stop (1296) rotate relative to each other. First tissue stop (1290) includes a first distal engagement surface (1291) and a top surface (1293). Second tissue stop (1296) includes a second distal engagement surface (1297) and a bottom surface (1298). If bottom surface (1298) overlaps with a portion of first tissue stop (1290) and top surface (1293) overlaps with a portion of second tissue stop (1296), first distal engagement surface (1291) and second distal engagement surface (1297) cooperate to prevent tissue from traveling to the proximal portion of end effector (1102).

However, if bottom surface (1298) does not overlap with a portion of first tissue stop (1290) and/or top surface does not overlap with a portion of second tissue stop (1296), then tissue may be captured between bottom surface (1298) and top surface (1293) at a proximal portion of end effector (1102). As mentioned above, detents (1206) may snap out of angle channels (1136) and into indicating recesses (1135), providing tactile feedback to the operator, when the operator rotates clamp pad assembly (1210) past the predetermined range of operating angles defined by angle channels (1136). This tactile feedback may also be dimensioned to correspond with first tissue stop (1290) and second tissue stop (1296) no longer overlapping with each other. In other words, when detents (1206) snap out of angle channels (1136) and into indicating recesses (1135), the corresponding tactile feedback may indicate to the operator that first tissue stop (1290) and second tissue stop (1296) are no longer overlapping. This may indicate to the operator that tissue may be captured between bottom surface (1298) and top surface (1293) at a proximal portion of end effector (1102) that is not capable of sufficiently simultaneously severing and sealing tissue.

Pivotable member (1170) also includes an integral heat shield (1175) in this example. Heat shield (1175) surrounds a portion of ultrasonic blade (1152). Heat shield (1175) may prevent ultrasonic blade (1152) from inadvertently contacting non-targeted tissue. Heat shield (1175) may include apertures (not shown) similar to apertures (176) described above. Apertures (not shown) may allow for undesired fluid and tissue to escape the confines of heat shield (1175) and ultrasonic blade (1152), as to not disturb the vibration of activated ultrasonic blade (1152). Additionally, heat shield (1175) may also include a distal bumper (not shown) similar to distal bumper (178). Such a distal bumper may be similar in function and configuration as distal bumper (178) described above.

E. Exemplary Button Cleaning

In some instances, it may be desirable to reuse handle assembly (1110) for multiple operations. If so, handle assembly (1110) may need to be cleaned and sterilized from operation to operation. However, buttons (1126) may obstruct areas of handle assembly (1110) and/or shaft assembly (1130) that need to be cleaned and sterilized. Therefore, it might be beneficial for buttons (1126) to transition to a position that provides access to otherwise covered portions of handle assembly (1110) and/or shaft assembly (1130). While the following example is explained using buttons (1126) and instrument (1000), it should be understand that these concepts and examples may be incorporated into buttons (126) and instrument (100), or any other instrument described herein.

Figure 19:
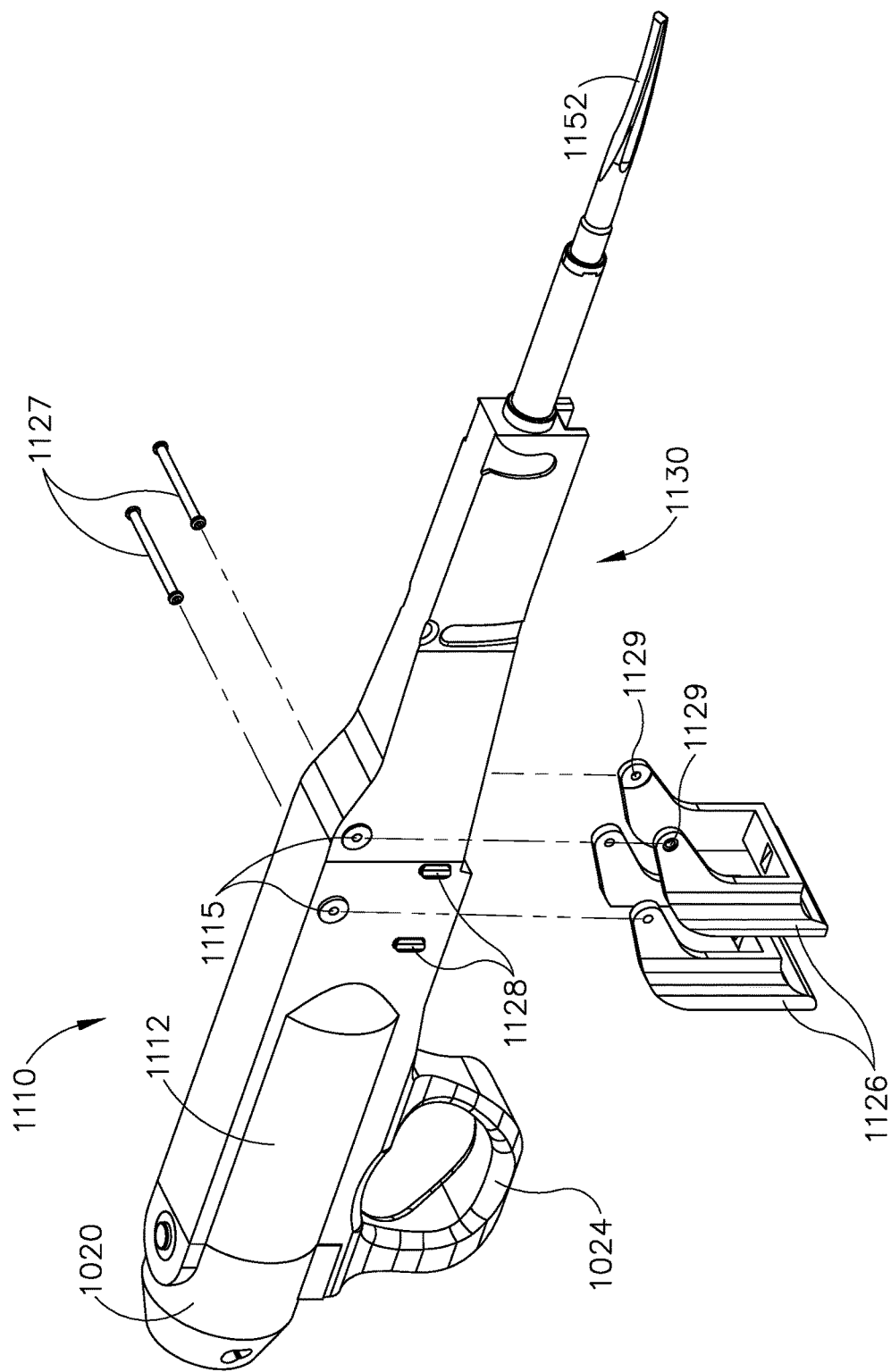
FIG. 19 depicts a perspective view of the handle assembly of the instrument of FIG. 11A, with triggers and pins separated from the remainder of the handle assembly.

As shown in FIG. 19, buttons (1126) define mounting holes (1129), which are configured to align with apertures (1115) defined by body (1112). Mounting pins (1127) are configured to travel through both apertures (1115) and mounting holes (1129) to rotationally fix buttons (1126) to handle assembly (1110). Handle assembly (1128) also includes detents (1128). As will be described in greater detail below, detents (1128) are configured to abut against buttons (1126) thereby acting as stops. Detents (1128) prevent buttons (1126) from inadvertent over-rotation.

Figure 20C:
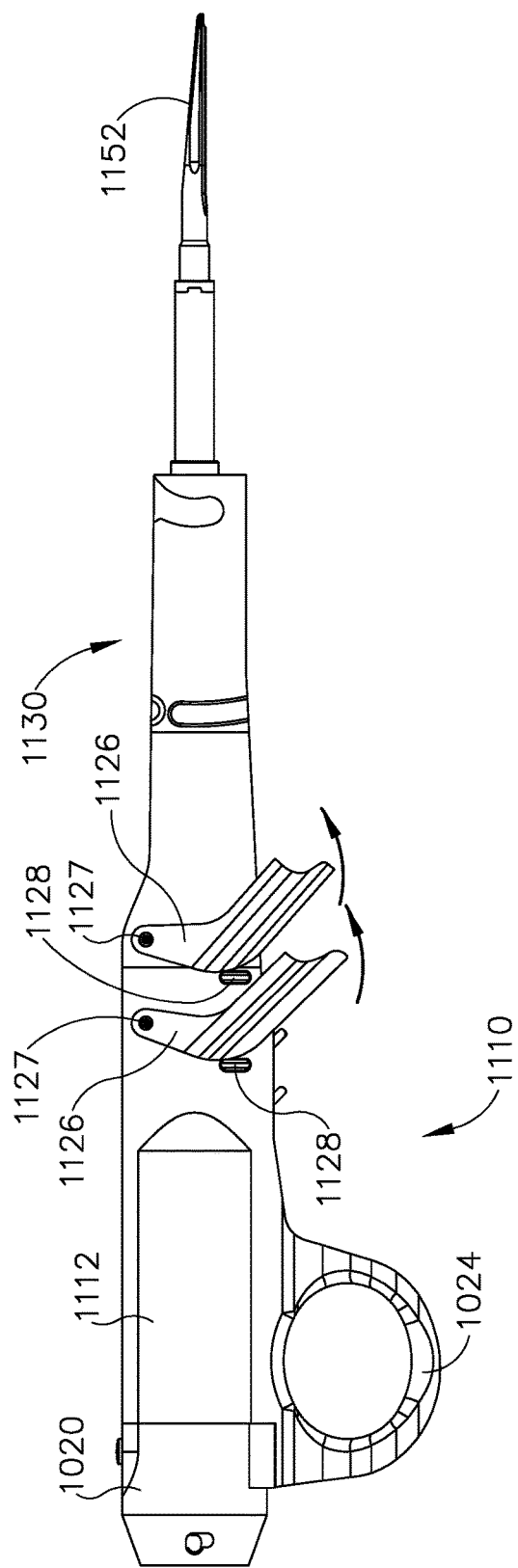
FIG. 20C depicts a side elevational view of the handle assembly of the instrument of FIG. 11A, with both of the triggers in respective third pivotal positions.

As shown in FIGS. 20A-20B, buttons (1126) may be pivoted proximally from a neutral position, as shown in FIG. 20A, to a firing position, as shown in FIG. 47B. In FIG. 20B, buttons (1126) are shown as rotating to the firing position together for purposes of illustration only. It should be understood that buttons (1126) may rotate independently of each other. While buttons (1126) are capable of rotating from the neutral position to the firing position, detents (1128) prevent buttons (1126) from inadvertently over rotating distally past the neutral position, in the opposite angular direction of the firing position. However, as mentioned above, when handle assembly (1110) is not in use, it may be desirable to clean and sanitize the portions of handle assembly (1110) that are covered by buttons (1126) in the neutral position, as shown in FIG. 20A. While detents (1128) may act as a stop from buttons (1126) inadvertently rotating distally past the positions shown in FIG. 20A, detents (1128) are sized such that the operator may apply enough rotational force in the opposite angular direction as the firing position such that buttons (1126) travel over detents (1128). In other words, buttons (1126) may be forced over detents (1128) to the position shown in FIG. 20C. When buttons (1126) are rotated to the position shown in FIG. 20C, the area of handle assembly (1110) originally covered by buttons (1126) in FIG. 20A is now exposed. Thus, the area originally covered by buttons (1126) in FIG. 20A is now accessible to clean. Additionally, detents (1128) prevent buttons (1126) from inadvertently returning to the neutral position as shown in FIG. 20A. Once cleaning is finished, an operator may snap buttons (1126) back over detents (1128) into the neutral position.

III. EXEMPLARY INSTRUMENT WITH CLAMP ANN HAVING COMPOUND LEVER ASSEMBLY

A. Overview

In some instances, it may be desirable to have the clamp pad assembly on the same side of the ultrasonic blade as the actuator that drives the clamp pad assembly. For instance, when dissecting the liver, it may be desirable to press the ultrasonic blade, while activated, into the liver and then rotate the clamp pad assembly toward the ultrasonic blade to dissect the liver parenchyma. Having the ultrasonic blade below the clamp pad assembly may give an operator better control and visualization of an instrument to perform the desired task.

Figure 21A:
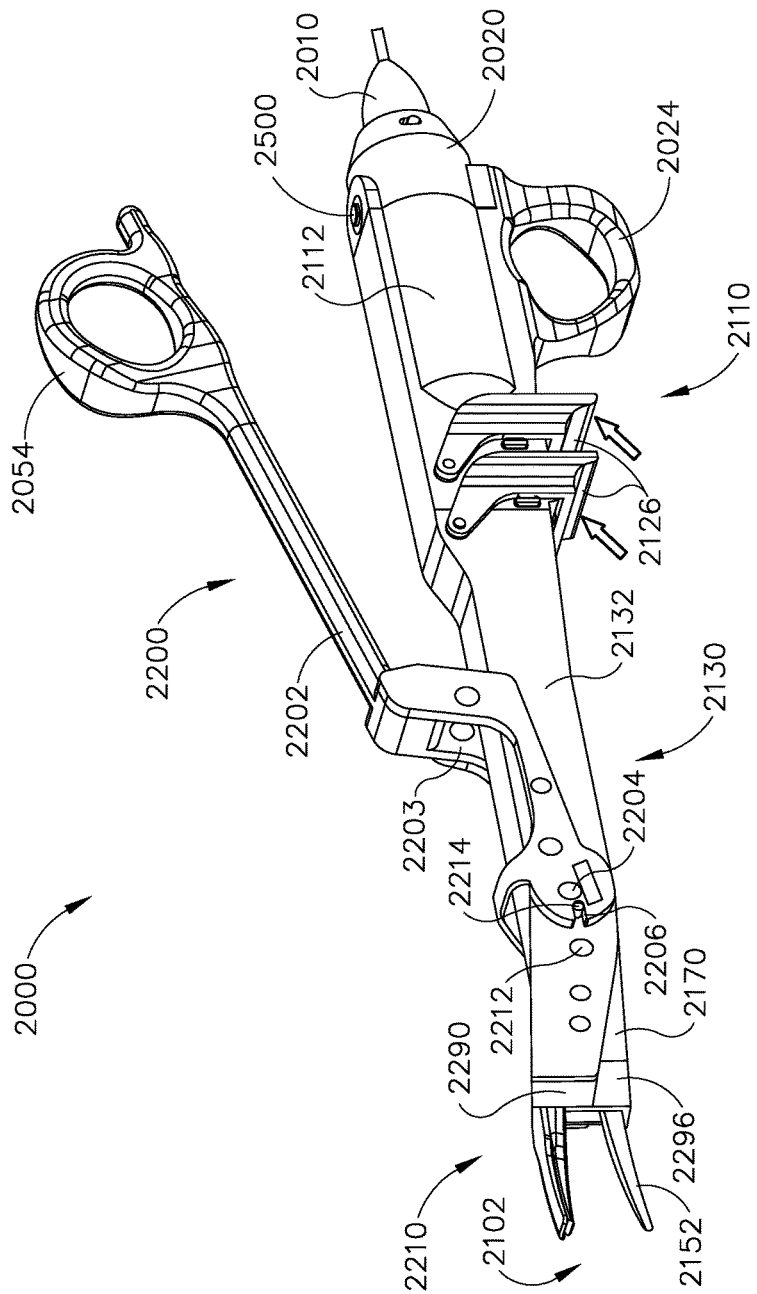
FIG. 21A depicts a perspective view of another exemplary surgical instrument, with an end effector of the instrument in an open configuration.
Figure 21B:
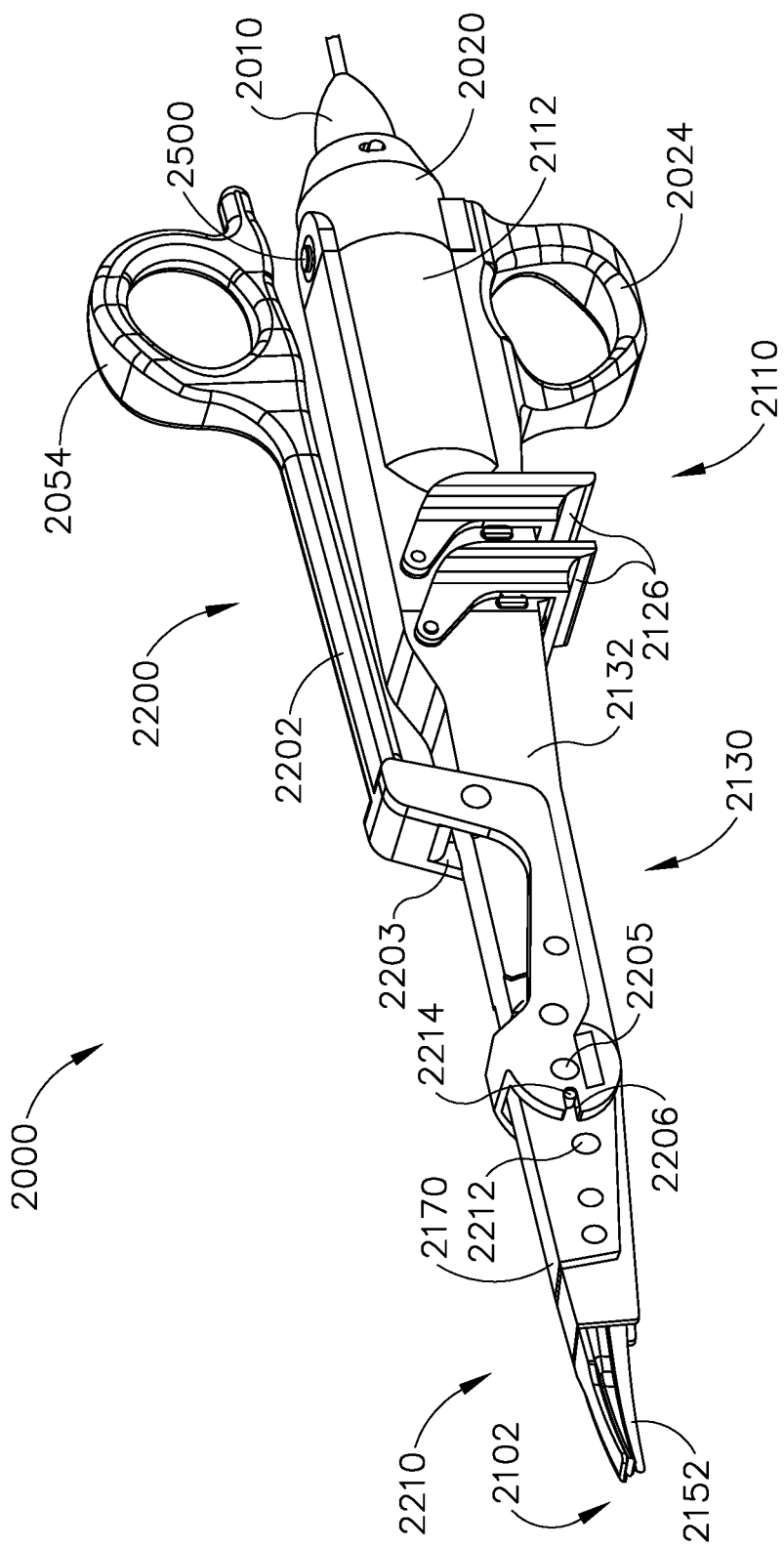
FIG. 21B depicts a perspective view of the instrument of FIG. 21A, with the end effector in a closed configuration.

FIGS. 21A-21B show instrument (2000) having a removable clamp arm assembly (2200), with a clamp pad assembly (2210) being located above ultrasonic blade (2152) and on the same side of instrument (2000) as thumb grip ring (2054). Instrument (2000) has an assembly similar to instrument (1000) except for the differences discussed below. It should be understood that instrument (2000) may be capable of delivering both ultrasonic energy and radio frequency (RF) energy to a surgical site in accordance with the teachings herein.

Instrument (2000) of this example comprises a plug (2010), a proximal casing (2020), handle assembly (2110), a shaft assembly (2130), an ultrasonic blade (2152) extending distally from shaft assembly (2130), a clamp arm assembly (2200), and an end effector (2102). As will be described in greater detail below, clamp arm assembly (2200) may be selectively attached to shaft assembly (2130) and detached from shaft assembly (2130). The ability to selectively attach and detach clamp arm assembly (2200) from shaft assembly (2130) may provide additional benefits of reusability for either handle assembly (2110) or clamp arm assembly (2200).

Handle assembly (2110) and shaft assembly (2130) are substantially the same as handle assembly (1110) and shaft assembly (1130) described above. For instance, handle assembly (2110) comprises a body (2112) including a finger grip ring (2024) and a pair of buttons (2126). Shaft assembly (2130) comprises an outer sheath (2132) extending distally from body (2112). It should therefore be understood that the primary differences between instrument (2000) and instrument (1000) are related to clamp arm assembly (2200).

Clamp arm assembly (2200) partially pivots toward and away from body (2112) of handle assembly (2110). Clamp arm assembly (2200) includes a body (2202) with a thumb grip ring (2054) and a Y-portion (2203). Thumb grip ring (2054) and finger grip ring (2024) together provide a scissor grip type of configuration. It should be understood, however, that various other suitable configurations may be used, including but not limited to a pistol grip configuration.

Figure 22A:
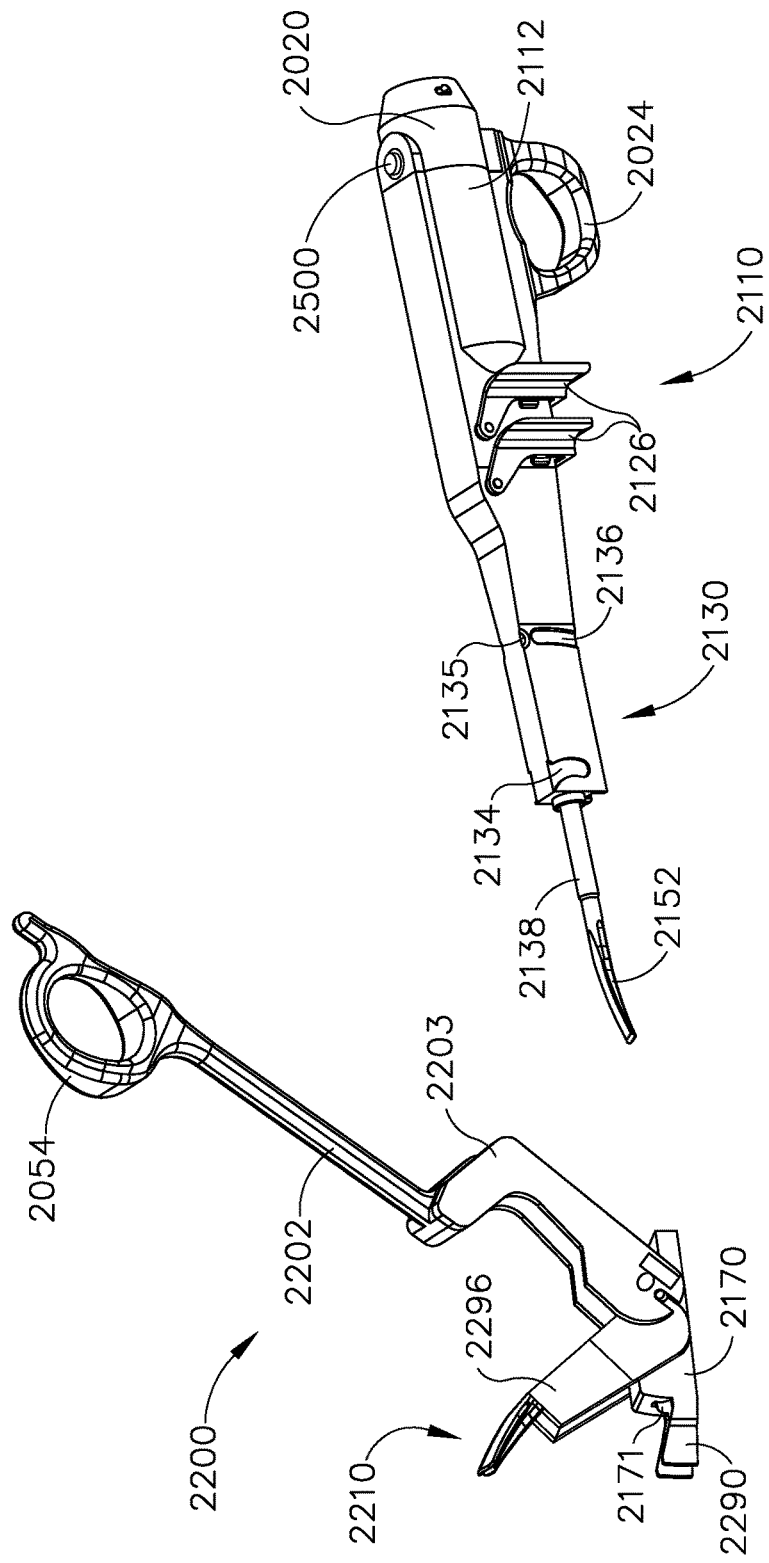
FIG. 22A depicts a perspective view of the instrument of FIG. 21A, with a clamp arm assembly separated from the handle assembly.
Figure 22B:
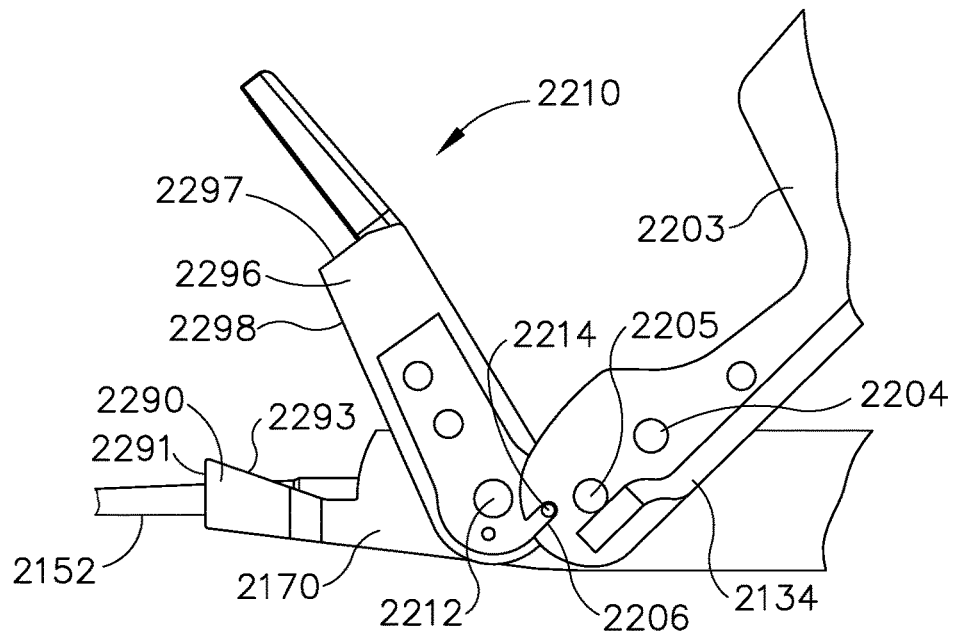
FIG. 22B depicts an enlarged side elevational view of a distal portion of the instrument of FIG. 21A, with the clamp arm assembly coupled with the handle assembly, and with the clamp arm assembly in a first pivotal state.

As best seen in FIGS. 22A-22B, end effector (2102) comprises an ultrasonic blade (2152) and a clamp pad assembly (2210). Ultrasonic blade (2152) extends distally from outer sheath (2132). Clamp arm assembly (2200) also comprises a receiving member (2170) and clamp pad assembly (2210). Receiving member (2170) defines a channel (2171) that is configured to receive ultrasonic blade (2152) and house tube (2138) of shaft assembly (2130). Y-portion (2203) is pivotally fixed to receiving member (2170) via pin (2205). Therefore, when receiving member (2170) houses tube (2138) of shaft assembly (2130), body (2202) of clamp arm assembly (2200) may rotate toward and away shaft assembly (2130) and housing assembly (2110).

Additionally, clamp pad assembly (2210) is pivotally fixed to receiving member (2170) via pin (2212). Clamp pad assembly (2210) is also connected to Y-portion (2203) between pins (2205, 2212) via a slot (2206) and pin (2214) connection. Clamp pad assembly (2210) and Y-portion (2203) thus form a compound lever assembly. Therefore, when body (2202) of clamp arm assembly (2200) rotates toward and away shaft assembly (2130) and housing assembly (2110) via pin (2205), slot (2206) and pin (2214) connection simultaneously rotate clamp pad assembly (2210) via pin (2212) in the opposite angular direction. For example, as seen in FIGS. 21A-21B, when thumb grip ring (2054) rotates body (2202) via pin (2204) toward handle assembly (2110), the distal end of clamp pad assembly (2210) rotates toward ultrasonic blade (2152). It should therefore be understood that an operator may squeeze thumb grip ring (2054) toward body (2112) to thereby clamp tissue between clamp pad assembly (2210) and ultrasonic blade (2152) to transect and/or seal the tissue. In some versions, one or more resilient members are used to bias clamp pad assembly (2210) to the open position shown in FIG. 21A. By way of example only, such a resilient member may comprise a leaf spring, a torsion spring, and/or any other suitable kind of resilient member.

B. Exemplary Assembly

Figure 22C:
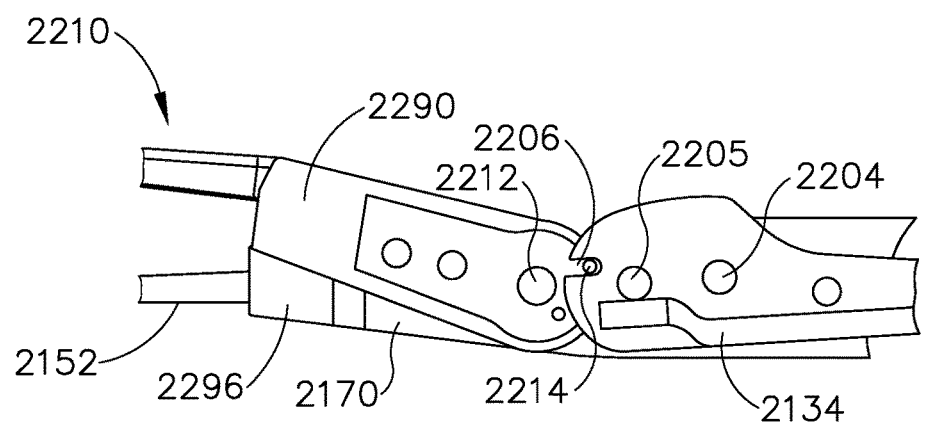
FIG. 22C depicts an enlarged side elevational view of a distal portion of the instrument of FIG. 21A, with the clamp arm assembly coupled with the handle assembly, and with the clamp arm assembly in a second pivotal state.

As mentioned above, clamp arm assembly (2200) may be attached and detached from handle assembly (2110). FIGS. 22A-22C show a process of coupling clamp arm assembly (2200) with handle assembly (2110). In particular, FIG. 22A shows clamp arm assembly (2200) decoupled from shaft assembly (2130) and handle assembly (2110). Y-portion (2203) of handle assembly (1200) includes a pair of protrusions (2204) that are configured to mate with shaft assembly (2130) after tube (2138) is housed within receiving member (2170). As shown in FIGS. 22B-22C, protrusions (2204) are positioned to enter actuate channels (2134) of shaft assembly (2130) when handle assembly (2200) rotates towards shaft assembly (2130). Once protrusions (2204) enter channels (2134), shaft assembly (2130) and clamp arm assembly (2200) may no longer translate relative to each other. In other words, protrusions (2204) and channels (2134) interact with each other to act as a locking mechanism for instrument (2000). Additionally, channels (2134) define a path of angular rotation in which clamp arm assembly (2200) may rotate relative to handle assembly (2110). In the case at hand, as shown in FIGS. 22B-22C, channels (2134) are long enough to allow clamp pad assembly (2210) to close against blade (2152).

C. Exemplary Tissue Stop

As mentioned above, in some instances, end effector (2102) may have a proximal portion that is not capable of sufficiently severing and sealing tissue. In such instances, it may be beneficial to provide for a tissue stop that may prevent tissue from traveling to these proximal portions of an end effector. As seen in FIGS. 22A-22C, Y-portion (2203) comprises a first tissue stop (2290) while receiving member (2170) comprises a second tissue stop (2296) Like first tissue stop (1290) and second tissue stop (1296) described above, first tissue stop (2290) and second tissue stop (2296) rotate relative to each other. First tissue stop (2290) includes a first engagement surface (2291) and a top surface (2293). Second tissue stop (2296) includes a second engagement surface (2297) and a bottom surface (2298). If distal end of bottom surface (2298) overlaps with a portion of first tissue stop (2290) and distal end of top surface (2293) overlaps with a portion of second tissue stop (2296), first engagement surface (2291) and second engagement surface (2297) cooperate to prevent tissue from traveling to the proximal portion of end effector (2102) that is not capable of sufficiently severing and sealing tissue.

However, if distal end of bottom surface (2298) does not overlap with a portion of first tissue stop (2290) and/or distal end of top surface does not overlap with a portion of second tissue stop (2296), then tissue may be captured between bottom surface (2298) and top surface (2293) at a proximal portion of end effector (2102) that is not capable of sufficiently severing and sealing tissue. Y-portion (2203) may have detents (not shown) similar to detents (1206) discussed above. These detents may snap out of angle channels (2136) into indicating recesses (2135), providing tactile feedback, when the operator rotates clamp pad assembly to a position corresponding with first tissue stop (2290) and second tissue stop (2296) not overlapping. In other words, when detents (not shown) snap out of angle channels (2136) and into indicating recesses (2135), the tactile feedback may indicate to the operator that first tissue stop (2290) and second tissue stop (2296) are no longer overlapping. This may indicate to the operator that tissue may be captured between bottom surface (2298) and top surface (2293) at a proximal portion of end effector (2102) that is not capable of sufficiently severing and sealing tissue.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade; and (d) a heat shield, wherein the heat shield is movable toward and away from the ultrasonic blade to thereby selectively shield a portion of the ultrasonic blade.

Example 2

The surgical instrument of Example 1, wherein the heat shield is configured to pivot toward and away from the ultrasonic blade.

Example 3

The surgical instrument of Example 2, wherein the heat shield is pivotable toward and away from the ultrasonic blade along a first plane, wherein the clamp arm is pivotable toward and away from the ultrasonic blade along the first plane.

Example 4

The surgical instrument of any one or more of Examples 1 through 3, wherein the heat shield is configured to approach a first lateral side of the ultrasonic blade, wherein the clamp arm is configured to approach a second lateral side of the ultrasonic blade.

Example 5

The surgical instrument of Example 4, wherein the second lateral side is opposite to the first lateral side.

Example 6

The surgical instrument of any one or more of Examples 1 through 5, wherein at least a portion of the heat shield includes a low friction material.

Example 7

The surgical instrument of Example 6, wherein the low friction material comprises polytetrafluoroethylene.

Example 8

The surgical instrument of any one or more of Examples 1 through 7, wherein the heat shield has a distal end including a protrusion, wherein the protrusion is configured to engage the ultrasonic blade and thereby space a remaining portion of the heat shield away from the ultrasonic blade.

Example 9

The surgical instrument of Example 8, wherein the protrusion comprises a low friction material.

Example 10

The surgical instrument of Example 9, wherein the low friction material comprises polytetrafluoroethylene.

Example 11

The surgical instrument of any one or more of Examples 1 through 10, wherein the heat shield defines a plurality of drainage openings.

Example 12

The surgical instrument of any one or more of Examples 1 through 11 in combination with the surgical instrument of any one or more of Examples 1 through 14.

Example 13

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade; and (d) a detent feature, wherein the detent feature is configured to provide tactile resistance to pivotal movement of the clamp arm relative to the body beyond a predefined pivot angle, wherein the detent feature is configured to permit pivotal movement of the clamp arm relative to the body beyond a predefined pivot angle upon application of a force sufficient to overcome the tactile resistance.

Example 14

The surgical instrument of Example 13, wherein the detent feature comprises a cantilevered member.

Example 15

A surgical instrument, comprising: (a) a body; (b) an ultrasonic blade extending distally from the body, wherein the ultrasonic blade is operable to apply ultrasonic energy to tissue; and (c) a clamp arm assembly pivotably coupled with the coupling post, wherein the clamp arm is operable to compress tissue against the ultrasonic blade, wherein the clamp arm assembly comprises (i) a clamp arm base, wherein the clamp arm base is configured to be secured to a distal end of the body, and (ii) a clamp arm pivotably coupled to the clamp arm base, wherein the clamp arm is operable to pivot toward the ultrasonic blade to thereby compress tissue against the ultrasonic blade while the clamp arm base is stationary relative to the body.

Example 16

The surgical instrument of Example 15, wherein the clamp arm assembly further comprises a detent assembly, wherein the detent assembly is configured to selectively maintain a first angular relationship between the clamp arm base and the clamp arm.

Example 17

The surgical instrument of Example 16, wherein the detent assembly is configured to selectively maintain a perpendicular relationship between the clamp arm base and the clamp arm when the clamp arm base is decoupled from the body.

Example 18

The surgical instrument of any one or more of Examples 15 through 17, wherein the clamp arm comprises a detent feature, wherein the body comprises a detent feature configured to complement the detent feature of the clamp arm, wherein the detent features of the clamp arm and the body are configured to selectively restrict pivotal movement of the clamp arm relative to the body when the clamp arm base is secured to the body.

Example 19

The surgical instrument of Example 18, wherein the detent feature of the body is positioned to be located proximal to the clamp arm base when the clamp arm base is secured to the body.

Example 20

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade; (d) a first tissue stop feature extending toward the clamp arm; and (e) a second tissue stop feature extending away from the clamp arm, wherein the second tissue stop feature is configured to pivot with the clamp arm, wherein the first and second tissue stop features are configured to restrict passage of tissue to proximal regions of the ultrasonic blade and clamp arm.

Example 21

The surgical instrument of Example 20, wherein a portion of the first tissue stop feature is positioned laterally relative to a portion of the second tissue stop feature.

Example 22

The surgical instrument of any one or more of Examples 20 through 21, wherein the first and second tissue stops are positioned to overlap with each other along a transverse path.

Example 23

The surgical instrument of any one or more of Examples 20 through 22, wherein the first tissue stop feature is configured to remain stationary relative to the clamp arm as the clamp arm pivots toward and away from the ultrasonic blade.

Example 24

The surgical instrument of any one or more of Examples 20 through 23, further comprising a heat shield, wherein the heat shield is configured to extend alongside at least a portion of the length of the ultrasonic blade and thereby shield the ultrasonic blade.

Example 25

The surgical instrument of Example 24, wherein the first tissue stop feature is secured to the heat shield.

Example 26

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade; and (d) an activation button, wherein the activation button is operable to pivot in a first pivotal direction from a neutral position to a triggering position to thereby trigger activation of the ultrasonic blade, wherein the activation is operable to pivot in a second pivotal direction from the neutral position to a cleaning position to thereby enable cleaning of a portion of the body.

Example 27

The surgical instrument of Example 26, further comprising a detent feature, wherein the detent feature is configured to resist pivotal movement of the trigger from the neutral position to the cleaning position.

Example 28

A surgical instrument, comprising: (a) a body; (b) an ultrasonic blade extending distally from the body, wherein the ultrasonic blade is operable to apply ultrasonic energy to tissue; (c) a clamp arm, wherein the clamp arm is operable to compress tissue against the ultrasonic blade; and (d) a pivot assembly, wherein the clamp arm is pivotably coupled to the body at the pivot assembly, wherein the pivot assembly comprises: (i) a first link, wherein the first link is pivotably coupled with the body at a first pivot, (ii) a second link, wherein the clamp arm is secured to the second link, wherein the second link is distal to the first link, wherein the second link is pivotably coupled with the first link at a second pivot, wherein the second pivot is distal to the first pivot, wherein the second link is further pivotably coupled with the body at a third pivot, wherein the third pivot is distal to the second pivot.

Example 29

The surgical instrument of Example 28, wherein the first link has a distal portion and a proximal portion, wherein the first and second pivots are located at the distal portion, wherein the proximal portion includes a grip feature configured to be engaged by an operator to thereby drive the proximal portion toward the body.

Example 30

The surgical instrument of any one or more of Examples 28 through 29, wherein a proximal portion of the first link is pivotable toward and away from the body along a first path, wherein the clamp arm is pivotable toward and away from the body along a second path, wherein the body defines a longitudinal axis, wherein the first and second paths are on the same side of the longitudinal axis.

Example 31

A surgical instrument, comprising: (a) a body; (b) an ultrasonic blade extending distally from the body, wherein the ultrasonic blade is operable to apply ultrasonic energy to tissue; (c) a clamp arm assembly comprising a clamp arm pivotably coupled with the body at a pivot assembly, wherein the clamp arm is operable to compress tissue against the ultrasonic blade; and (d) a detent assembly, wherein the detent assembly is configured to provide tactile resistance to pivotal movement of the clamp arm relative to the body beyond a predefined pivot angle, wherein the detent assembly is configured to permit pivotal movement of the clamp arm relative to the body beyond a predefined pivot angle upon application of a force sufficient to overcome the tactile resistance.

Example 32

The surgical instrument of Example 31, wherein the detent assembly comprises a cantilevered member.

Example 33

The surgical instrument of any one or more of Examples 31 through 32, wherein the clamp arm assembly further comprises a clamp arm base, wherein the clamp arm base is configured to be secured to a distal end of the body, wherein the clamp arm is pivotably coupled to the clamp arm base, wherein the clamp arm is operable to pivot toward the ultrasonic blade to thereby compress tissue against the ultrasonic blade while the clamp arm base is stationary relative to the body.

Example 34

The surgical instrument of Example 33, wherein the detent assembly is configured to selectively maintain a first angular relationship between the clamp arm base and the clamp arm.

Example 35

The surgical instrument of Example 34, wherein the detent assembly is configured to selectively maintain a perpendicular relationship between the clamp arm base and the clamp arm when the clamp arm base is decoupled from the body.

Example 36

The surgical instrument of any one or more of Examples 33 through 35, wherein detent assembly comprises: (i) a clamp arm detent feature on the clamp arm, and (ii) a body detent feature on the clamp arm, wherein the body detent feature is configured to complement the clamp arm detent feature, wherein the clamp arm detent feature and the body detent feature are configured to selectively restrict pivotal movement of the clamp arm relative to the body when the clamp arm base is secured to the body.

Example 37

The surgical instrument of Example 36, wherein the body detent feature is positioned to be located proximal to the clamp arm base when the clamp arm base is secured to the body.

Example 38

The surgical instrument of any one or more of Examples 31 through 37, further comprising: (a) a first tissue stop feature extending toward the clamp arm; and (b) a second tissue stop feature extending away from the clamp arm, wherein the second tissue stop feature is configured to pivot with the clamp arm, wherein the first and second tissue stop features are configured to restrict passage of tissue to proximal regions of the ultrasonic blade and clamp arm.

Example 39

The surgical instrument of Example 38, wherein a portion of the first tissue stop feature is positioned laterally relative to a portion of the second tissue stop feature.

Example 40

The surgical instrument of any one or more of Examples 38 through 39, further comprising a heat shield, wherein the heat shield is configured to extend alongside at least a portion of the length of the ultrasonic blade and thereby shield the ultrasonic blade.

Example 41

The surgical instrument of Example 40, wherein the first tissue stop feature is secured to the heat shield.

Example 42

The surgical instrument of any one or more of Examples 31 through 41, further comprising an activation button, wherein the activation button is operable to pivot in a first pivotal direction from a neutral position to a triggering position to thereby trigger activation of the ultrasonic blade, wherein the activation is operable to pivot in a second pivotal direction from the neutral position to a cleaning position to thereby enable cleaning of a portion of the body.

Example 43

The surgical instrument of Example 42, further comprising a detent feature, wherein the detent feature is configured to resist pivotal movement of the trigger from the neutral position to the cleaning position.

Example 44

The surgical instrument of any one or more of Examples 31 through 43, further comprising a clamp arm actuator, wherein the clamp arm actuator is located on a first side of a longitudinal axis defined by the body, wherein the clamp arm is located on a second side of the longitudinal axis defined by the body, wherein the first side is opposite to the second side.

Example 45

The surgical instrument of any one or more of Examples 31 through 44, further comprising a clamp arm actuator, wherein the clamp arm actuator is located on a first side of a longitudinal axis defined by the body, wherein the clamp arm is also located on the first side of the longitudinal axis defined by the body.

Example 46

A surgical instrument, comprising: (a) a body; (b) an ultrasonic blade extending distally from the body, wherein the ultrasonic blade is operable to apply ultrasonic energy to tissue; (c) a clamp arm, wherein the clamp arm is operable to compress tissue against the ultrasonic blade; and (d) a pivot assembly, wherein the clamp arm is pivotably coupled to the body at the pivot assembly, wherein the pivot assembly comprises: (i) a first link, wherein the first link is pivotably coupled with the body at a first pivot, and (ii) a second link, wherein the clamp arm is secured to the second link, wherein the second link is distal to the first link, wherein the second link is pivotably coupled with the first link at a second pivot, wherein the second pivot is distal to the first pivot, wherein the second link is further pivotably coupled with the body at a third pivot, wherein the third pivot is distal to the second pivot.

Example 47

The surgical instrument of Example 46, wherein the first link has a distal portion and a proximal portion, wherein the first and second pivots are located at the distal portion, wherein the proximal portion includes a grip feature configured to be engaged by an operator to thereby drive the proximal portion toward the body.

Example 48

The surgical instrument of any one or more of Examples 46 through 47, wherein a proximal portion of the first link is pivotable toward and away from the body along a first path, wherein the clamp arm is pivotable toward and away from the body along a second path, wherein the body defines a longitudinal axis, wherein the first and second paths are on the same side of the longitudinal axis.

Example 49

A surgical instrument, comprising: (a) a body; (b) an ultrasonic blade extending distally from the body, wherein the ultrasonic blade is operable to apply ultrasonic energy to tissue; (c) a clamp arm assembly, comprising: (i) a receiving member, wherein the receiving member is configured to longitudinally receive a distal portion of the body along a longitudinal axis shared by the body and the receiving member, (ii) a clamp arm pivotably coupled with the receiving member by a first pivot, and (iii) a clamp arm actuator pivotably coupled with the receiving member by a second pivot, wherein the clamp arm is further pivotably coupled with the receiving member by a third pivot.

Example 50

The surgical instrument of Example 49, wherein the first pivot is located at a first longitudinal position, wherein the second pivot is located at a second longitudinal position, wherein the third pivot is located at a third longitudinal position, wherein the first longitudinal position is distal to the second and third longitudinal positions, wherein the second longitudinal position is proximal to the first and second longitudinal positions

V. MISCELLANEOUS

It should be understood that the various teachings herein may be readily combined with the various teachings of U.S. patent application Ser. No. 15/284,819, entitled "Surgical Instrument with Dual Mode End Effector and Side-Loaded Clamp Arm Assembly," filed on Oct. 4, 2016, published as U.S. Pub. No. 2017/0105754 on Apr. 20, 2017, issued as U.S. Pat. No. 10,893,914 on Jan. 19, 2021, the disclosure of which is incorporated by reference herein. Various suitable ways in which the teachings herein may be combined with the teachings of U.S. patent application Ser. No. 15/284,819, filed Oct. 4, 2016, published as U.S. Pub. No. 2017/0105754 on Apr. 20, 2017, issued as U.S. Pat. No. 10,893,914 on Jan. 19, 2021, will be apparent to those of ordinary skill in the art.

It should be understood that the various teachings herein may be readily combined with the various teachings of U.S. patent application Ser. No. 15/284,855, entitled "Surgical Instrument with Dual Mode End Effector and Modular Clamp Arm Assembly," filed on Oct. 4, 2016, published as U.S. Pub. No. 2017/0105788 on Apr. 20, 2017, the disclosure of which is incorporated by reference herein. Various suitable ways in which the teachings herein may be combined with the teachings of U.S. patent application Ser. No. 15/284,855, filed Oct. 4, 2016, published as U.S. Pub. No. 2017/0105788 on Apr. 20, 2017, will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) an ultrasonic blade extending distally from the body, wherein the ultrasonic blade is operable to apply ultrasonic energy to tissue;
   (c) a clamp arm assembly comprising a clamp arm pivotably coupled with the body at a pivot arm, wherein the clamp arm is operable to pivotally move in a first direction relative to the pivot arm along an arcuate path within a predefined pivot angle to compress tissue against the ultrasonic blade; and
   (d) a detent assembly, wherein the detent assembly is configured to provide tactile resistance to pivotal movement of the clamp arm relative to the body in a second direction of movement opposite the first direction along the arcuate path beyond the predefined pivot angle, wherein the detent assembly is configured to permit pivotal movement of the clamp arm in the second direction relative to the body beyond the predefined pivot angle upon application of a force sufficient to overcome the tactile resistance.

2. The surgical instrument of claim 1, wherein the detent assembly comprises a cantilevered member.

3. The surgical instrument of claim 1, wherein the clamp arm assembly further comprises a clamp arm base, wherein the clamp arm base is configured to be secured to a distal end of the body, wherein the clamp arm is pivotably coupled to the clamp arm base, wherein the clamp arm is operable to pivot toward the ultrasonic blade to thereby compress tissue against the ultrasonic blade while the clamp arm base is stationary relative to the body.

4. The surgical instrument of claim 3, wherein the detent assembly is configured to selectively maintain a first angular relationship between the clamp arm base and the clamp arm.

5. The surgical instrument of claim 4, wherein the detent assembly is configured to selectively maintain a perpendicular relationship between the clamp arm base and the clamp arm when the clamp arm base is decoupled from the body.

6. The surgical instrument of claim 3, wherein the detent assembly comprises:
   (i) a clamp arm detent feature on the clamp arm, and
   (ii) a body detent feature on the body, wherein the body detent feature is configured to complement the clamp arm detent feature, wherein the clamp arm detent feature and the body detent feature are configured to selectively restrict pivotal movement of the clamp arm relative to the body when the clamp arm base is secured to the body.

7. The surgical instrument of claim 6, wherein the body detent feature is positioned to be located proximal to the clamp arm base when the clamp arm base is secured to the body.

8. The surgical instrument of claim 1, further comprising:
(a) a first tissue stop feature extending toward the clamp arm; and
(b) a second tissue stop feature extending away from the clamp arm, wherein the second tissue stop feature is configured to pivot with the clamp arm, wherein the first and second tissue stop features are configured to restrict passage of tissue to proximal regions of the ultrasonic blade and the clamp arm.

9. The surgical instrument of claim 8, wherein a portion of the first tissue stop feature is positioned laterally relative to a portion of the second tissue stop feature.

10. The surgical instrument of claim 8, further comprising a heat shield, wherein the heat shield is configured to extend alongside at least a portion of the length of the ultrasonic blade and thereby shield the ultrasonic blade.

11. The surgical instrument of claim 10, wherein the first tissue stop feature is secured to the heat shield.

12. The surgical instrument of claim 1, further comprising an activation button, wherein the activation button is operable to pivot in a first pivotal direction from a neutral position to a triggering position to thereby trigger activation of the ultrasonic blade, wherein the activation is operable to pivot in a second pivotal direction from the neutral position to a cleaning position to thereby enable cleaning of a portion of the body.

13. The surgical instrument of claim 12, further comprising a detent feature, wherein the detent feature is configured to resist pivotal movement of the activation button from the neutral position to the cleaning position.

14. The surgical instrument of claim 1, further comprising a clamp arm actuator, wherein the clamp arm actuator is located on a first side of a longitudinal axis defined by the body, wherein the clamp arm is located on a second side of the longitudinal axis defined by the body, wherein the first side is opposite to the second side.

15. The surgical instrument of claim 1, wherein the detent assembly further includes a detent, a first recess that is positioned along the arcuate path within the predefined pivot angle, and a second recess positioned along the arcuate path outside of the predefined pivot angle, wherein the detent assembly is configured to provide tactile feedback when the detent is pivotably moved in the first direction from the second recess to the first recess, and provides tactile feedback when the detent is pivotably moved in the second direction from the first recess to the second recess.

16. A surgical instrument, comprising:
(a) a body including a shaft;
(b) an ultrasonic blade extending distally from the body, wherein the ultrasonic blade is operable to apply ultrasonic energy to tissue;
(c) a clamp arm assembly operable to compress tissue against the ultrasonic blade;
(d) a detent; and
(e) an arcuate channel,
wherein the arcuate channel is configured to pivotably mate with the detent to define an arcuate path of angular rotation in which the clamp arm assembly pivotally rotates relative to the body, and
wherein the detent and the arcuate channel are respectively positioned on the clamp arm assembly and the shaft, or
wherein the detent and the arcuate channel are respectively positioned on the shaft and clamp arm assembly,
wherein the clamp arm assembly is removably coupled with the shaft and further includes a clamp arm pivotably coupled to a pivotal arm, wherein the pivotal arm is configured to longitudinally slide over the shaft during assembly.

17. The surgical instrument of claim 16, wherein the shaft includes the arcuate channel configured to mate with the detent to longitudinally lock the clamp arm assembly to the shaft.

18. The surgical instrument of claim 16, wherein the shaft is configured to be affixed within the pivotal arm when assembled.

19. A surgical instrument of claim 18, wherein the clamp arm includes the detent.

20. A surgical instrument, comprising:
(a) a body;
(b) an ultrasonic blade extending distally from the body, wherein the ultrasonic blade is operable to apply ultrasonic energy to tissue;
(c) a clamp arm assembly including a clamp arm pivotably coupled with the body at a pivot arm, wherein the clamp arm is operable to pivotally move in a first direction relative to the body to compress tissue against the ultrasonic blade;
(d) a first tissue stop feature extending distally and transversely relative to the clamp arm, wherein the first tissue stop is configured to stop tissue from moving proximally;
(e) a second tissue stop feature extending distally and transversely from the pivot arm, wherein the second tissue stop is configured to prevent tissue from moving proximally, wherein the second tissue stop feature overlaps the first tissue stop feature within a predefined pivot angle to prevent tissue from being captured between the first and second tissue stop features; and
(f) a detent assembly, wherein the detent assembly is configured to provide tactile feedback to indicate to an operator that the clamp arm has pivotally moved relative to the pivot arm beyond the predefined pivot angle thereby allowing tissue to be captured between the first and second tissue stop features.

* * * * *